United States Patent
Harris et al.

(10) Patent No.: US 8,270,563 B2
(45) Date of Patent: Sep. 18, 2012

(54) DIAGNOSTIC SCANNING APPARATUS

(75) Inventors: Timothy Andrew Harris, Calgary (CA); Jeffrey Russell Smithanik, Calgary (CA); Daren Paul Tremaine, Silverton (CA)

(73) Assignee: Aktiebolaget SKF, Göteborg (SE)

( * ) Notice: Subject to any disclaimer, the term of this patent is extended or adjusted under 35 U.S.C. 154(b) by 300 days.

(21) Appl. No.: 12/833,498

(22) Filed: Jul. 9, 2010

(65) Prior Publication Data

US 2011/0194669 A1    Aug. 11, 2011

Related U.S. Application Data

(60) Provisional application No. 61/302,859, filed on Feb. 9, 2010.

(51) Int. Cl.
*G01N 23/00* (2006.01)
(52) U.S. Cl. .......................... 378/15; 378/197
(58) Field of Classification Search ............... 378/4–20, 378/193, 196, 197
See application file for complete search history.

(56) References Cited

U.S. PATENT DOCUMENTS

| | | | |
|---|---|---|---|
| 5,196,748 A | 3/1993 | Rigney | |
| 5,268,955 A | 12/1993 | Burke et al. | |
| 5,305,363 A * | 4/1994 | Burke et al. | 378/4 |
| 5,493,599 A * | 2/1996 | Mattson | 378/147 |
| 5,548,629 A | 8/1996 | Kimura et al. | |
| 6,276,145 B1 * | 8/2001 | Sharpless et al. | 62/51.1 |
| 6,404,845 B1 * | 6/2002 | Sharpless et al. | 378/15 |
| 6,563,244 B1 | 5/2003 | Yamauchi et al. | |
| 6,748,806 B2 | 6/2004 | Halsmer | |
| 7,023,952 B2 | 4/2006 | Brunnett | |
| 7,277,523 B2 | 10/2007 | Mattson | |
| 2007/0153977 A1 | 7/2007 | Yokoyama et al. | |

FOREIGN PATENT DOCUMENTS

WO    2010/026523 A2    3/2010
WO    2012/006527 A1    1/2012

OTHER PUBLICATIONS

International Search Report and Written Opinion dated Oct. 31, 2011 for child International application No. PCT/US2011/043365.

* cited by examiner

*Primary Examiner* — Hoon Song
(74) *Attorney, Agent, or Firm* — Mark A. Ussai

(57) ABSTRACT

An apparatus includes an annular rotor that rotates about a rotational axis. A magnetic bearing system influences the position of the annular rotor in three-dimensional space and includes at least three actuators, wherein at least one actuator generates a force for lifting the annular rotor in a vertical direction, at least one actuator influences the position of the annular rotor in the radial direction of the annular rotor and at least assists in maintaining an annular gap between at least one non-magnetic bearing and the annular rotor during operation and at least one actuator influences the position of the annular rotor in an axial direction of the annular rotor. At least one radiation source may be fixedly mounted on the annular rotor.

26 Claims, 10 Drawing Sheets

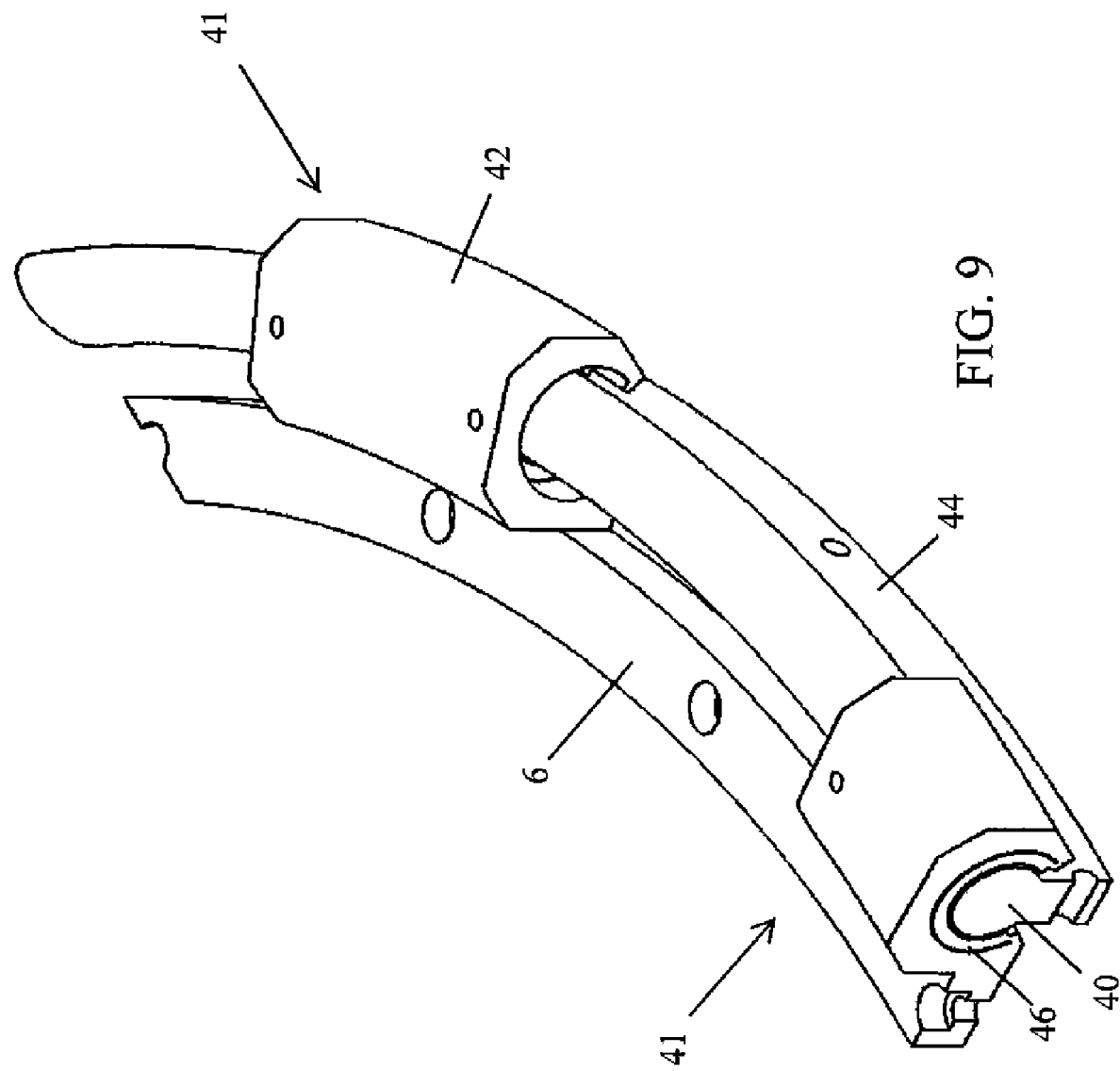

DIAGNOSTIC SCANNING APPARATUS

CROSS-REFERENCE

This application claims priority to U.S. patent application No. 61/302,859 filed Feb. 9, 2010, the contents of which are fully incorporated herein by reference.

TECHNICAL FIELD

The present teachings generally relate to a diagnostic scanning apparatus, such as a computed tomography imaging system, having one or more magnetic bearings for rotatably supporting an annular rotor or gantry. The present teachings also relate more generally to arrangements for rotatably supporting an annular rotor, which rotates, e.g., in a substantially vertical or horizontal plane, using one or more magnetic bearings.

BACKGROUND ART

Known computed tomography (CT) imaging systems include a rotatable annular gantry or rotor having a gantry bore for receiving a patient or other object to be internally imaged. In typical CT applications, an x-ray source is mounted on the annular gantry and radiates a fan-shaped, wedge-shaped, or cone-shaped x-ray beam in the plane of gantry rotation. The x-ray beam passes through the patient while the annular gantry is rotating and the attenuated x-rays are sensed by a detector array disposed on the gantry opposite to the x-ray source.

Thus, while the annular gantry is rotating, a series of x-ray projections or 2-D slices of the patient are obtained at different angles. These projections are mathematically reconstructed to create a tomographic image of each slice. The patient may be moved axially through the bore to obtain data on adjacent slices and the slices may be combined to generate a 3-D image of interest.

Generally speaking, higher rotational speeds are desired in order to reduce the time required to obtain the tomographic image of interest and/or to provide high-speed or "freeze motion" images. However, higher rotational speeds often lead to problems with respect to the static and dynamic balance of the rotating annular gantry.

In the past, it has been attempted to maintain the balance of the gantry by setting very tight tolerances for the center of gravity and the masses of the components mounted on the gantry. These components generally include the x-ray source and detector, signal processing circuitry, power supplies and cooling systems. The gantry may then be manually balanced by adding and adjusting balancing weights, which is a time consuming and difficult task.

Thus, the need to dynamically offset any imbalances arising during operation has required relatively complex solutions, such as the solution described in U.S. Pat. No. 6,748,806, which changes the position of movable weights disposed on the annular gantry during operation to maintain the dynamic balance of the annular gantry.

Further, if it becomes necessary to replace or service the mechanical bearings supporting the gantry, subsequent field rebalancing is more difficult than balancing at the time of manufacturing and also leads to a loss of valuable usage time for the system. In addition, the re-application of lubricants, e.g., bearing grease, in a sterile environment such as a medical facility is also problematic.

U.S. Pat. No. 7,277,523 mentions the use of high speed mechanical bearings, air bearings, magnetic beatings, or the like to rotatably support the annular gantry, but provides no details concerning the construction of the bearings. U.S. Pat. No. 7,023,952 discloses air bearings for rotatably supporting the annular gantry of a diagnostic scanning device.

SUMMARY

It is an object of the present disclosure to provide an improved diagnostic scanning apparatus, e.g., an improved computed tomography imaging system.

In addition or in the alternative, it is an object of the present disclosure to provide improved designs for rotatably supporting an annular rotor using a magnetic bearing system or arrangement.

In one aspect of the present teachings, a magnetic bearing arrangement for a rotor is disclosed, which uses the concept of magnetic levitation to lift and/or to rotatably support the rotor so that it can rotate in a friction-free manner. The rotor is preferably designed to rotate about a substantially horizontal axis, such that the radial direction of the rotor is in a vertical or substantial vertical plane. However, such a system can also be designed to permit tilting of the rotational axis, e.g., by +/−30° or more.

In another aspect of the present teachings, the rotor may rotate about a vertical axis or a substantially vertical axis, which again may be tiltable, e.g., by +/−30° or more.

In another aspect of the present teachings, an apparatus preferably includes a rotor that rotates about a rotational axis. A magnetic bearing system influences the position of the annular rotor in three-dimensional space and may include at least three actuators, such as at least one actuator that generates a force for lifting the annular rotor in a vertical direction, at least one actuator that influences the position of the annular rotor in the radial direction of the rotor and at least assists in maintaining an annular gap between at least one non-magnetic bearing and the annular rotor in the radial direction during operation and at least one actuator that influences the position of the annular rotor in an axial direction of the rotor. The lift actuator may be combined with one of the radial actuator and/or the axial actuator, such that, e.g., the radial actuator also performs a rotor-lifting function and/or the axial actuator also performs a rotor-lifting function.

Such an apparatus may further comprise at least one radiation source mounted on the rotor such that the apparatus is configured for scanning and/or imaging applications.

In further aspects of the present teachings, the following, non-limiting embodiments are disclosed:

1. An apparatus comprising:

an annular rotor comprising, at least in part, a magnetically-permeable material disposed on or proximal to an outer circumference thereof, the rotor being rotatable about a rotational axis, at least one non-magnetic bearing disposed adjacent to the annular rotor and capable of rotatably supporting the annular rotor at least temporarily, wherein the outer circumference of the annular rotor has a diameter slightly less than the diameter of a radially-inward-facing surface of the non-magnetic bearing and a magnetic bearing system disposed adjacent to the outer circumference of the annular rotor, the magnetic bearing system comprising:

at least one lift actuator generating a magnetic field and being fixedly disposed adjacent to a vertically upper portion of the annular rotor, the at least one lift actuator being configured to generate a force that lifts the annular rotor in a vertical direction at least while the annular rotor is rotating about the rotational axis, at least one radial actuator generating a variable magnetic field and being fixedly disposed adjacent to the outer circumference of the annular rotor, the at least one radial actuator being configured to influence the position of the annular rotor in the radial direction of the annular rotor while the annular rotor is rotating so as to maintain an annular clearance between the radially-inward-facing surface of the at least one non-magnetic bearing in the radial direction and the outer circumference of annular rotor, and at least one axial actuator generating a variable magnetic field and being fixedly disposed adjacent to the annular rotor, the at least one axial actuator being configured to influence the position of the annular rotor in an axial direction of the rotor.

2. An apparatus as in embodiment 1, wherein the rotational axis extends substantially in a horizontal direction, but is preferably tiltable by up to about +/−30 degrees.

3. An apparatus comprising:

a rotor configured to be rotated about a rotational axis, a magnetic bearing system configured to influence the position of the annular rotor in three-dimensional space and including at least three actuators, wherein:

at least one lift actuator is configured to generate a force for lifting the rotor in a vertical direction, at least one radial actuator is configured to influence the position of the rotor in the radial direction of the rotor and to at least assist in maintaining an annular gap between the annular rotor and at least one non-magnetic bearing disposed around an outer circumference of the annular rotor in the radial direction of the annular rotor while the annular rotor is rotating under the control and/or guidance of the magnetic bearing system, and at least one axial actuator is configured to influence the position of the annular rotor in an axial direction of the rotor.

4. An apparatus comprising:

a stationary housing having a bore defined therein, an annular rotor rotatably disposed within the bore of the stationary housing and comprising, at least in part, a magnetically-permeable material on a surface adjacent to the bore of the stationary housing, the rotor being rotatable about a rotational axis extending in an at least substantially horizontal direction, at least one lift actuator configured to generate a magnetic field and being mounted on the stationary housing adjacent to a generally upper portion of the bore, the at least one lift actuator being configured to generate a force that lifts the annular rotor within the central bore in a radial direction of the rotor at least while the annular rotor rotates, at least one radial actuator configured to generate a variable magnetic field and being mounted on the stationary housing adjacent to a generally lower portion of the bore, the at least one radial actuator being configured to influence the position of the annular rotor within the central bore in the radial direction of the rotor, wherein the at least one lift actuator and the at least one radial actuator are configured to influence the position of the annular rotor while it rotates to maintain an annular spacing around the annular rotor in the radial direction thereof, and at least one axial actuator configured to generate a variable magnetic field and being mounted on the stationary housing proximal to the bore, the at least one axial actuator being configured to influence the position of the annular rotor within the central bore in an axial direction of the rotor.

5. An apparatus as in any preceding embodiment, wherein the at least one radial actuator and/or the at least one axial actuator comprise at least one electromagnet configured to generate the variable magnetic field, and/or wherein the at least one radial actuator and/or the at least one axial actuator comprise a permanent magnet.

6. An apparatus as in any preceding embodiment, wherein the at least one lift actuator is fixedly mounted adjacent to a vertically uppermost portion of the rotor.

7. An apparatus as in any preceding embodiment, wherein the at least one lift actuator comprises at least one permanent magnet configured to lift at least 50%, more preferably at least 70% and even more preferably at least 80% of the weight of the rotor.

8. An apparatus as in any preceding embodiment, wherein the at least one lift actuator comprises an electromagnet configured to generate a variable magnetic field.

9. An apparatus as in any preceding embodiment, wherein the annular rotor includes an annular flange comprising, at least in part, a magnetically-permeable material, the annular flange being disposed within a gap defined in the at least one axial actuator.

10. An apparatus as in any preceding embodiment, wherein the apparatus comprises at least three axial actuators fixedly disposed around the annular rotor, preferably equidistantly or substantially equidistantly, the annular flange being disposed within respective, radially-extending spacings defined in each of the axial actuators.

11. An apparatus as in embodiment 10, wherein at least one of the axial actuators is disposed adjacent to a vertically lowermost portion of the annular rotor.

12. An apparatus as in any preceding embodiment, wherein the apparatus comprises at least three radial actuators disposed around the outer circumference of the rotor, optionally disposed in a mirror-symmetric manner about a vertical plane that contains an ideal rotational axis of the annular rotor.

13. An apparatus as in any preceding embodiment, wherein the at least one lift actuator comprises at least one of a passive homopolar actuator, an active homopolar actuator, a passive heteropolar actuator or an active heteropolar actuator.

14. An apparatus as in any preceding embodiment, wherein the radial and axial actuators each comprise an active heteropolar actuator and/or an active homopolar actuator.

15. An apparatus as in any preceding embodiment, wherein the rotor comprises a laminated magnetically-permeable material and the radial actuator(s) comprise(s) a heteropolar actuator.

16. An apparatus as in any preceding embodiment, wherein the rotor has an outer diameter that is greater than its longitudinal length, the rotor outer diameter preferably being at least 2 times greater than the longitudinal length, more preferably at least 5 times greater than the longitudinal length, even more preferably at least 8 times greater than the longitudinal length and still more preferably at least 10 times greater than the longitudinal length.

17. An apparatus as in any preceding embodiment, wherein the rotor has a hollow interior, optionally sized to receive a patient therein.

18. An apparatus as in any preceding embodiment, wherein the at least one radial actuator is replaced with a non-magnetic bearing for rotatably supporting the rotor in the radial direction of the rotor, the non-magnetic bearing optionally being, e.g., a plain bearing or a roller-element bearing.

19. An apparatus as in any one of embodiments 1-17, wherein the at least one axial actuator is replaced with a non-magnetic bearing for guiding the rotor in the axial direction of the rotor, the non-magnetic bearing optionally being, e.g., a plain bearing or a roller-element bearing.

20. An apparatus as in any preceding embodiment, further comprising at least one position sensor configured to detect the position of the rotor in the radial and/or axial directions.

21. An apparatus as in any one of embodiments 4-20, further comprising at least one auxiliary, non-magnetic bearing mounted on the stationary housing and being configured to support the annular rotor, e.g., at least when the annular rotor is not rotating, and/or to rotatably support the annular rotor at least temporarily, e.g., during a fault in the magnetic bearing system.

22. An apparatus as in embodiment 21, wherein the auxiliary, non-magnetic bearing is a curved ball bearing affixed to one of the rotor or the stationary housing and a ring shaft is movably disposed within the curved ball bearing, the ring shaft being affixed to the other of the rotor and the stationary housing.

23. An apparatus as in embodiment 22, wherein the outer diameter of the ring shaft is slightly less than the inner diameter of the curved ball bearing, so that the ring shaft does not contact the curved ball bearing when the rotor is being rotated under the guidance of the magnetic bearings.

24. An apparatus comprising:
an annular rotor having an annular flange extending in a radial direction of the annular rotor, the annular rotor comprising, at least in part, a magnetically-permeable material on or adjacent to at least one circumferential surface and the annular rotor being rotatable about a rotational axis,
at least one non-magnetic bearing disposed adjacent an outer circumference of the annular rotor,
at least one radial actuator disposed adjacent to a generally outer circumferential portion of the annular rotor, the at least one radial actuator being controllable to influence the position of the annular rotor in a plane perpendicular to rotational axis while the annular rotor rotates so as to maintain an annular gap between the at least one non-magnetic bearing and the annular rotor in the radial direction, and
at least three axial actuators disposed around the circumference of the annular rotor, the annular flange being disposed within a spacing defined in each of the axial actuators, each axial actuator comprising an electromagnet configured to influence the position of the annular gantry in an axial direction of the annular rotor.

25. An apparatus as in embodiment 24, further comprising one or more additional features or additional sub-features of the above-embodiments 1-23.

26. An apparatus as in any preceding embodiment, wherein the at least one non-magnetic bearing is selected from a plain bearing and a rolling-element bearing.

27. An apparatus as in any one of embodiments 26, wherein the at least one non-magnetic bearing comprises a curved tubular structure having recirculating balls disposed on an inner surface thereof and configured to receive a torus-shaped structure therein.

28. An apparatus as in embodiment 27, wherein the balls recirculate in a closed path that extends or lies in the radial direction of the torus-shaped structure.

29. An apparatus as in embodiment 27 or 28, wherein the balls comprise a ceramic material.

30. An apparatus as in any one of embodiments 27-29, wherein two or more closed paths for recirculating balls are defined on the inner surface of the curved tubular structure, more preferably four or more closed paths, even more preferably six or more closed paths.

31. An apparatus as in any preceding embodiment, wherein the apparatus is a diagnostic scanning apparatus and further comprises a radiation source mounted on the rotor so as to rotate therewith.

32. An apparatus as in embodiment 31, further comprising a radiation detector mounted on the rotor generally opposite of the radiation source.

33. An apparatus as in embodiment 31 or 32, wherein the apparatus is a computed tomography image system and the radiation source is an x-ray source.

34. A method of scanning, imaging or treating a patient or an object comprising:
rotating the annular rotor of the apparatus of any one of embodiments 31-33 and
actuating the radiation source to irradiate the patient or the object.

35. A method as in embodiment 34, further comprising detecting attenuated radiation signals after passing through or being scattered by the patient or the object being scanned or imaged.

Certain advantages may result due to the construction and/or arrangement of one or more of the above-identified embodiments or of other embodiments disclosed herein, including but not limited to:

(i) improved reliability and/or reduced maintenance, which provides more operational time for the machine, thereby improving productivity, (ii) reduced noise and/or vibration, which may make the machine less intimidating for an operator or patient, and which may also serve to further improve reliability and service life, (iii) greater tolerance of unbalance in the rotor system due to the capability of the magnetic bearing system to compensate for unbalance during operation by adjusting magnetic forces generated by one or more of the actuators, which may reduce the necessary manufacturing tolerances for balancing purposes and thus also may reduce manufacturing costs and/or service costs for re-balancing, (iv) avoiding or reducing problems inherent to roller bearings, which require a defined clearance-play with narrow manufacturing tolerance, (v) automatic adjustment of the gantry/rotor location in three-dimensional space in real-time through electronic control, rather than through mechanical adjustments to the rotor/gantry and/or the mechanical bearings supporting the gantry/rotor, which must be made when the system is not operating, (vi) reduced or no lubrication requirements, thereby minimizing or eliminating the amount of grease that must be used, e.g., in a sterile environment, such as a hospital or other medical facility, and/or (vi) increased rotational speeds, which may help to reduce the time necessary to collect the necessary scanning images and thereby reduce the patient's or object's exposure to the radiation source and/or may help to obtain high speed images in order to freeze motion (i.e. generate images with little or no motion blur), such as when scanning a beating heart.

It is understood that the claims of the patent as granted may provide none, one or more of the above-identified advantages and/or may provide one or more advantages not explicitly mentioned herein.

Further embodiments, advantages, features and details of the present teachings are derivable from the following description of the exemplary embodiments in view of the Figures.

BRIEF DESCRIPTION OF THE DRAWINGS

FIG. 9 shows a perspective view of a portion of the curved bearing arrangement of FIGS. 8A and 8B.

DETAILED DESCRIPTION OF THE INVENTION

Each of the additional features and teachings disclosed below may be utilized separately or in conjunction with other features and teachings to provide improved bearings for annular rotors and/or bearing assemblies and/or diagnostic scanning systems, as well as methods for designing, constructing and using the same. Representative examples of the present invention, which examples utilize many of these additional features and teachings both separately and in combination, will now be described in further detail with reference to the attached drawings. This detailed description is merely intended to teach a person of skill in the art further details for practicing preferred aspects of the present teachings and is not intended to limit the scope of the invention. Therefore, combinations of features and steps disclosed in the following detail description may not be necessary to practice the invention in the broadest sense, and are instead taught merely to particularly describe representative examples of the present teachings.

Moreover, the various features of the above Summary section, the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

Figure 1:
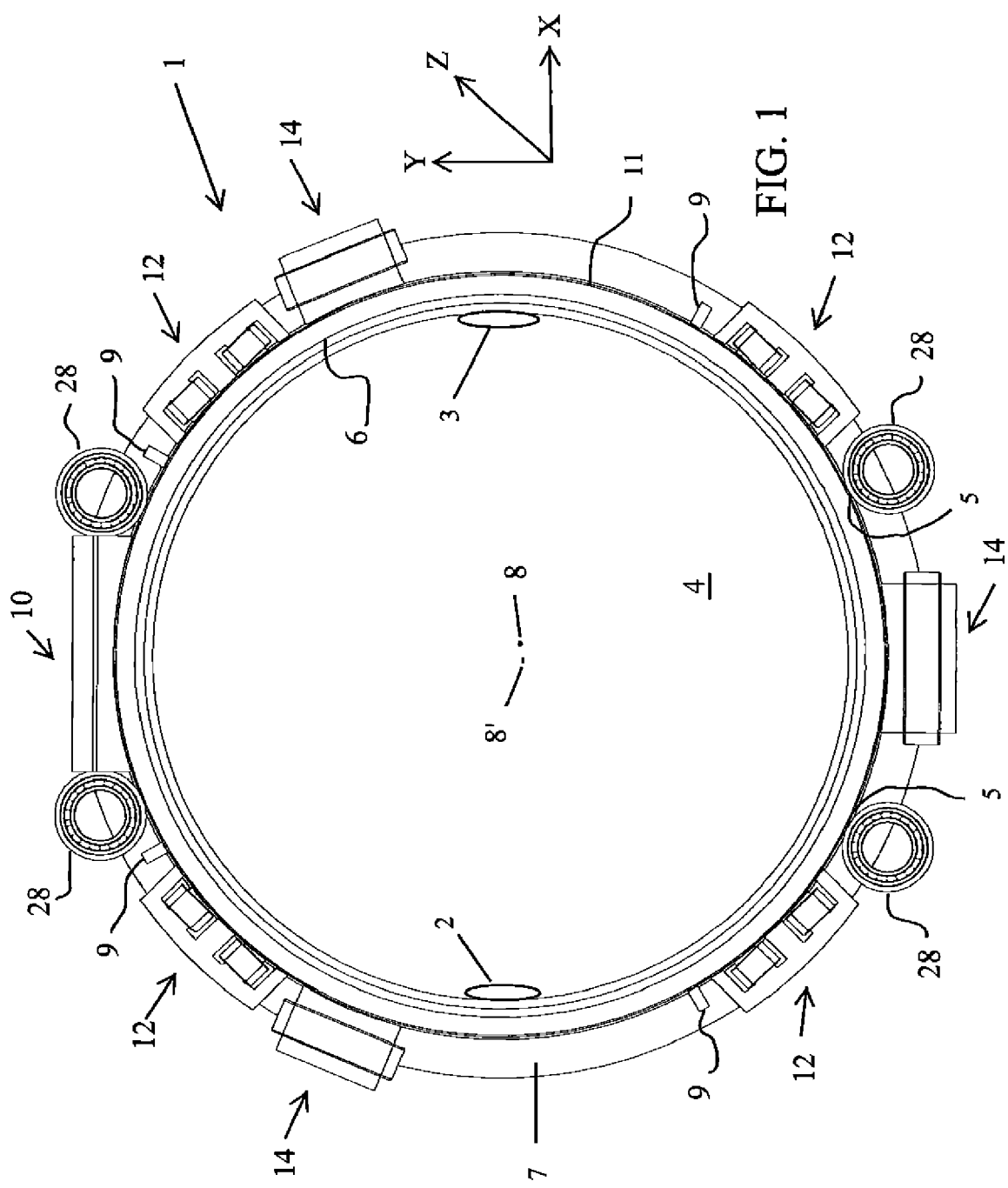
FIG. 1 shows an elevation view of a first representative embodiment of the present teachings.

FIG. 1 shows a side view of a first representative bearing arrangement for a ring-shaped rotor, which may be used, e.g., in a computed tomography (CT) machine 1. As indicated by the directional arrows on the right side of the drawing, the sheet of the drawing represents an X-Y plane and a Z-axis extends perpendicular to the sheet of the drawing, i.e. perpendicular to the X-Y plane.

Generally speaking, the computed tomography machine 1 may include a stationary gantry housing (not shown) having a central bore extending along the Z-axis. A patient table may be inserted into the bore and moved along the Z-axis in order to scan a patient or other object lying on the table. The bore preferably has a diameter of at least one meter in preferred CT applications. However, the diameter of the bore depends upon the particular application of the present teachings and various bore diameters may be utilized. Also, as discussed below, the magnetic bearing arrangements disclosed herein are not limited to diagnostic scanning apparatus and may be used in other rotor applications. The CT machine 1 is simply a suitable embodiment for describing particular aspects of the present teachings in further detail.

A rotor or annular gantry 6 is rotatably disposed within the stationary gantry housing. The rotor 6 preferably has a substantially tubular shape in three-dimensional view, i.e. it has a hollow interior 4. The hollow interior 4 is concentric with the bore of the gantry housing, such that a patient or other object to be scanned can be placed within the hollow interior 4 of the rotor 6 during the imaging operation.

The radial direction of the rotor 6 is disposed substantially in the vertical, X-Y plane, which is the imaging plane, and the axial direction of the rotor 6 extends in the Z-direction. During operation, the rotor 6 rotates about a rotational axis 8 that extends in the horizontal or Z-direction, such that the rotor 6 rotates within the plane X-Y, i.e. the radial direction of the rotor 6 falls within a substantially vertical plane. However, the rotational plane of the rotor 6 is preferably tiltable from the vertical plane, such that the rotor 6 may rotate in a plane that preferably deviates from the vertical plane by up to about +/−30°, although greater degrees of tilt are also contemplated by the present teachings.

As will be further discussed below, an annular gap or clearance 5 exists between one or more non-magnetic or auxiliary bearing(s) 28 and the rotor 6 when the rotor 6 is rotating under the influence or guidance of the magnetic bearing system, so that a friction-free bearing of the rotor 6 is possible.

The rotor 6 has an outer circumference 11 with a diameter that is preferably slightly less than an inner diameter of the non-magnetic bearing(s) 28 disposed around the rotor 6, such that an annular gap 5 in the range of about 0.25-1.5 millimeters exists during operation and thus the overall magnetic gap is about 0.5-3.0 millimeters. However, it is preferred that the annular gap 5 is as small as possible during rotation of the rotor 6 and smaller annular gaps 6 are understood to fall within the present teachings. The size of the annular gap 5 is determined, in principle, by the manufacturing tolerances of the rotor 6, and is sized just big enough so that the rotor 6 preferably or normally does not contact any stationary part of the housing or bearing(s) 28 during normal operation.

In one embodiment, a motor may rotatably drive the rotor 6, e.g., via a gear system or a belt looped around the rotor 6. In other embodiments, the rotor 6 may be rotatably driven by a direct-drive motor, wherein the rotor of the direct-drive motor has the same or substantially the same size/diameter as the rotor 6 of the CT machine 1 and the motor rotor is directly coupled or connected to the rotor 6 of the CT machine 1.

In preferred CT applications of the present teachings, the rotor 6 supports one or more components necessary to generate the computed tomography images. For example, one or more of the following devices may be mounted on the rotor 6 so as to rotate therewith: an x-ray tube (more generally, radiation source 2) and its collimation mechanism, an x-ray detector (more generally, radiation detector 3), a data acquisition system, power supplies and cooling systems, which are well known in the art and need not be described in detail herein. Generally speaking, the components are located on the rotor 6 so that their mass and centers of gravity are substantially statically and dynamically balanced when the rotor 6 is rotating at its normal rotational speed. Precise dynamic and static balancing is normally not obtainable at desired levels of manufacturing tolerances both in the components and their placement on the rotor 6. In one optional aspect of the present teachings, dynamic imbalances may be correctable in real-time during operation by adjusting the magnetic fields of one or more types of actuators 10, 12, 14 disposed around the rotor 6.

A radiation source 2 may be mounted on the rotor 6 of FIG. 1 so that the radiation source 2 rotates together with the rotor 6. A radiation detector or detector array 3, which is configured to sense or detect attenuated radiation after it has passed through an object (e.g., a patient) located in the hollow interior 4, may be mounted on an opposite side of the rotor 6. In the alternative, a stationary detector array may be mounted on or around the stationary gantry housing, so that the detector array does not rotate with the rotor 6. As indicated above, various other types of components will ordinarily be mounted on the rotor 6, but the details of such other types of components are not particularly pertinent to the present teachings.

The various components mounted on the rotating rotor 6 may communicate with a stationary CT controller (not shown), e.g., via one or more slip rings that enable the interchange of data and power. In addition or in the alternative, communications may take place wirelessly between the components mounted on the rotor 6 and the CT controller. The CT controller optionally may also control the motor and/or the magnetic bearings (i.e. at least radial and axial actuators 12, 14), or a separate magnetic bearing controller may be provided. The CT controller processes signals from the imaging components and generates CT images for the user in a manner well known in the art.

In the first representative embodiment, which will be described now in more detail with reference to FIGS. 1-4, the rotor 6 is rotatably and axially guided by three types of magnetic bearings that will be referred to herein as actuators. Because magnetic bearings provide non-contacting rotation, they minimize maintenance and eliminate the need for lubricants.

More specifically, at least one lift actuator 10, at least one radial actuator 12 and at least one axial actuator 14 are mounted on the gantry housing at fixed locations relative to the rotatable rotor 6. As will be understood, the actuators 10, 12, 14 are capable of generating magnetic fields that influence the position of rotor 6 in the three-dimensional space (X, Y and Z directions). Thus, the rotor 6 comprises, at least in part, a magnetically-permeable material (i.e. a material attracted to a magnetic field), such as, but not-limited to, a ferrous material. At least the radial and axial actuators 12, 14 are preferably capable of producing a variable magnetic field, but the lift actuator 10 also may be optionally configured to produce a variable magnetic field, as will be discussed in the second representative embodiment below.

Figure 2:
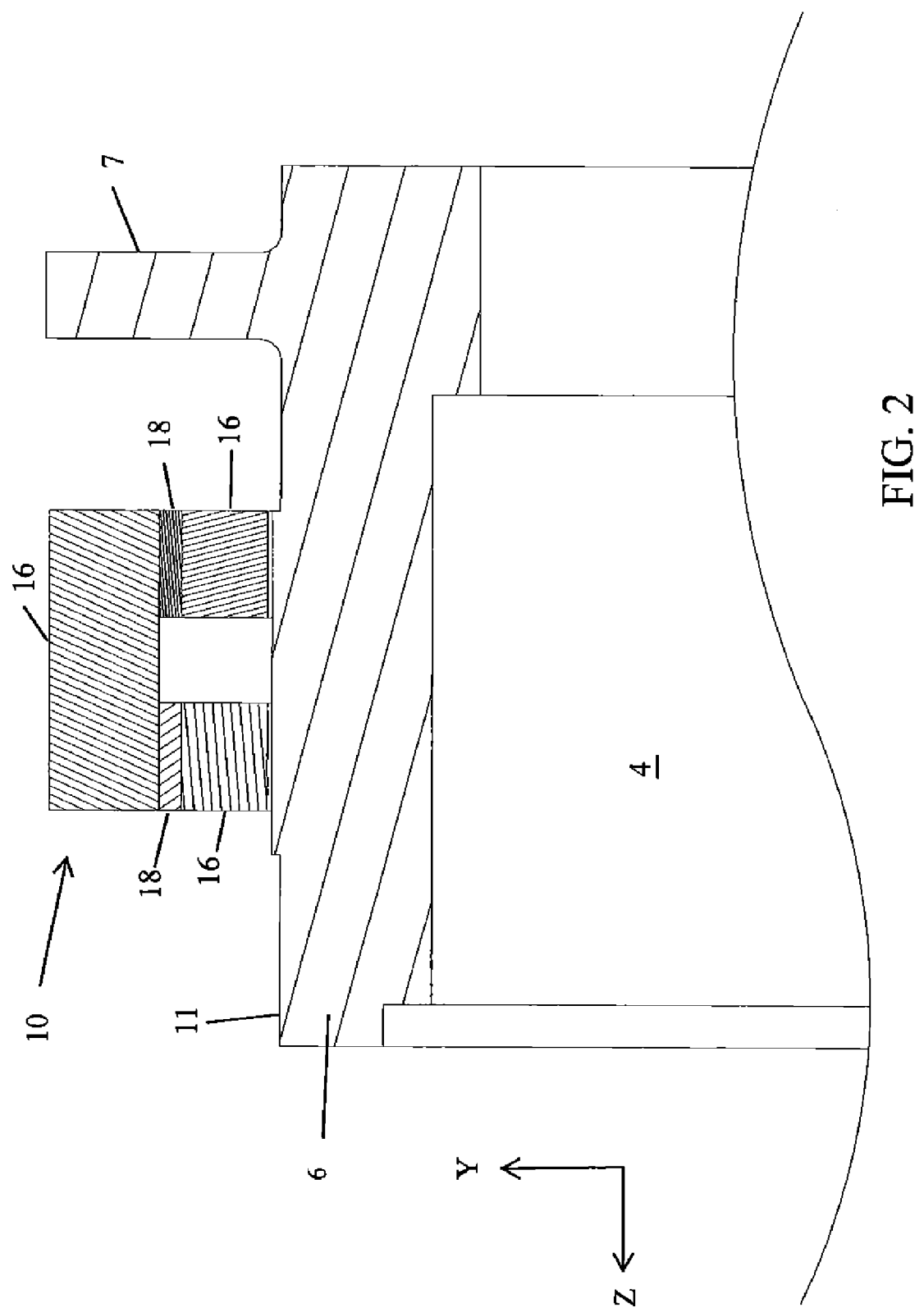
FIG. 2 shows a detailed cross-sectional view of a lift actuator shown in FIG. 1.

The at least one lift actuator 10 is preferably disposed at or adjacent to a vertically uppermost portion of the rotor 6, e.g., at the top of the X-Y plane. Referring to FIG. 2, the lift actuator 10 preferably comprises a stator core 16 and at least one permanent magnetic 18. Although the lift actuator 10 is given a reference number different from the radial actuators 12 in the present embodiment, it is understood that the lift actuator 10 may be simply a modified version of the radial actuator 12 and/or the lift actuator 10 may be replaced by a radial actuator 12 in certain embodiments, as will be further discussed below.

In CT applications of the present teachings, the weight of the rotor 6 with all the components mounted thereon may be relatively high, e.g., about 1000 kilograms. Thus, in such applications, it is cost-effective to utilize at least one permanent magnetic 18 to perform the bulk or majority of the rotor-lifting work during operation for maintaining the annular gap 5 between the rotor 6 and the auxiliary bearing(s) 28. Thus, the permanent magnet 18 may be utilized to increase the overall system efficiency by reducing the load requirement on the electromagnet portions of the actuators 10 and 12 that influence the position of the rotor 6 in the radial direction thereof, i.e. in the X-Y plane.

For example, the permanent magnet 18 may be sized and selected, in a particularly preferred embodiment, such that it is capable of lifting at least about 90% of the weight of the rotor 6. More generally, the permanent magnet 18 may be sized and selected such that it is capable of lifting between about 50-150% of the weight of the rotor 6, more preferably between about 70-130%, even more preferably between about 80-120%. If the lift actuator 10 is capable of lifting 100% or more of the weight of the rotor 6, then the radial actuator(s) 12 operate, in part, to pull the rotor 6 away from the lift actuator 10 during operation, so as to maintain the annular gap 5 between the rotor 6 and the non-magnetic bearing(s) 28 disposed adjacent to the lift actuator 10. In addition or in the alternative, the lift actuator 10 may include an electromagnet configured to generate a variable magnetic field that cancels or offsets a portion of the magnetic flux generated by the permanent magnet 18, thereby giving the lift actuator 10 an overall lesser lifting capacity during operation.

Although not shown in FIG. 2, the magnetic flux path of the lift actuator 10 is a closed path, e.g., a substantially circular path, that extends generally in the Y-Z plane and goes through the various portions of the stator core 16, though the permanent magnets 18, across a clearance or gap between the rotor 6 and the stator core 16 and though the adjacent portion of the rotor 6.

As will be understood, the lift actuator 10 need not contain a permanent magnet and the entire rotor-lifting work may be performed by one or more electromagnets, for example, an electromagnet according to one of the radial actuators 12 discussed below. Further, in certain embodiments, the lift actuator 10 can be completely omitted and replaced by two or more radial actuators 12, each of which may or may not comprise a permanent magnet.

In the alternative, the lift actuator 10 may be both passive and active, i.e. it may include at least one permanent magnet and at least one coil so that it is also an electromagnet, as will be discussed below with respect to the embodiment of FIG. 6.

As with all of the directional actuators 10, 12, 14, the functionality of the actuators can be divided so that some actuators are only permanent magnets (i.e. no coil) and some actuators are only electromagnets (e.g., only a coil/stator core arrangement). For example, a single actuator disclosed herein as having both a permanent magnet and an electromagnet may be separated into two separate actuators to perform the respective passive and active magnetic functions.

Referring back to FIG. 1, four radial actuators 12 may be mounted on the gantry housing and are disposed around the circumference of the rotor 6. As will be discussed further below, the number of radial actuators 12 is variable according to the present teachings and may be more or less than four. However, generally speaking, between two to five radial actuators 12 are particularly preferred.

Figure 3:
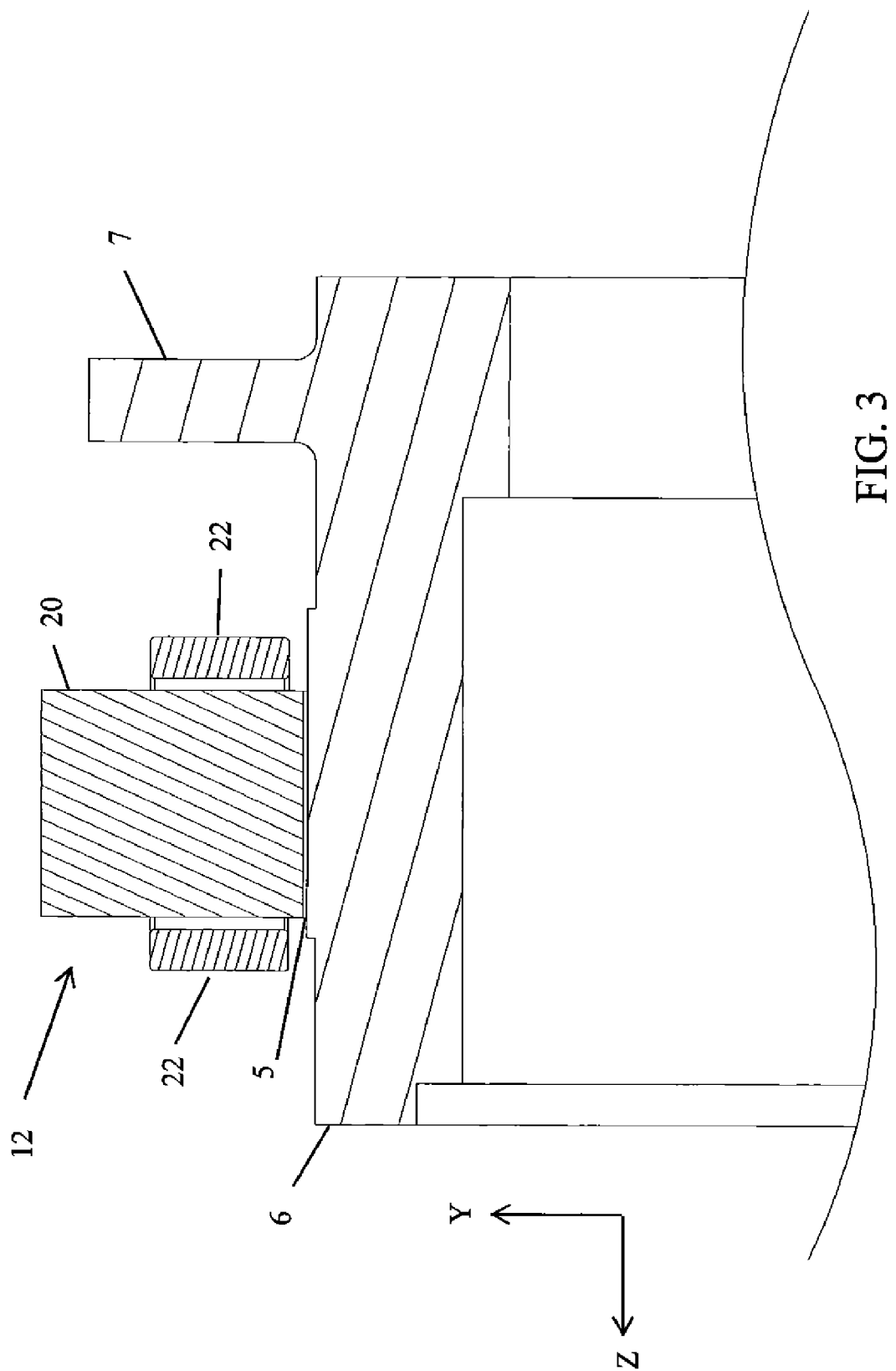
FIG. 3 shows a detailed cross-sectional view of a radial actuator shown in FIG. 1.

FIG. 3 shows a representative radial actuator 12 according to the first embodiment in greater detail. This radial actuator 12 comprises an electromagnet having at least one stator core 20 and at least one coil 22 wound around the core 20. Although the radial actuator 12 of this embodiment does not include a permanent magnet, such a design modification is possible. Further, although the cross-sectional drawing of FIG. 3 shows only a single core 20 and a single coil 22, each radial actuator 12 may comprise one or more coils 22 wound around one or more cores 20, as is shown in FIG. 1.

The radial actuators 12 are designed to adjust the position of the rotor 6 relative to the non-magnetic or auxiliary bearing(s) 28 in the X-Y plane during operation, i.e. in the radial direction of the rotor 6. Therefore, the radial actuators 12 are operated or controlled to ensure that the annular gap 5 is an appropriate distance or radial length while the rotor 6 is rotating, so that the rotor 6 does not contact the auxiliary bearing(s) 28. This ensures a friction-free rotation of the rotor 6 during operation.

For example, referring to FIG. 1, an ideal rotational axis 8' may be defined within the central bore of the gantry housing and preferably extends in the Z-direction. The ideal rotational axis 8' defines an axis of rotation that would provide an optimal or ideal spacing of the annular gap 5 between the rotor 6 and auxiliary bearing(s) 28 during operation. The respective radial actuators 12 are preferably individually controlled (as well as also lift actuator 10 if it optionally contains an electromagnet). In this case, the strength of the magnetic field generated by each respective radial actuator 12 is variably adjusted (as well as also lift actuator 10 if it optionally contains an electromagnet), such that the actual rotational axis 8 of the rotor 6 is aligned, or is substantially aligned, with the ideal rotational axis 8' during operation. That is, deviations between the actual and ideal rotational axes 8, 8' in the X-Y plane can be corrected or minimized by applying magnetic fields of different strengths to the rotor 6 via the radial actuators 12 (10), thereby pulling the rotor 6 in the appropriate direction to eliminate the deviation or at least substantially reduce the deviation.

Because the lift actuator 10 of this embodiment comprises only a passive magnetic source (i.e. permanent magnet 18), it is not actively controlled. However, the position of the rotor 6 in the X-Y plane is controlled or determined by the respective magnetic forces generated by the lift actuator 10 and the radial actuators 12. As was indicated above, if the lift actuator 10 includes a coil, then the lift actuator 10 will also actively participate in controlling the X-Y position of the rotor 6.

It should be understood that the distance between the ideal rotational axis 8' and the actual rotational axis 8 shown in FIG. 1 has been exaggerated for illustration purposes and is not to scale. In practice, the distance between the two axes 8, 8' is preferably equal to or less than about one millimeter.

At least a portion of the circumferential outer portion of the rotor 6 that is disposed adjacent to the lift actuator(s) and the radial actuator(s) 12 comprises a magnetically-permeable material. Further, because the two radial actuators 12 disposed on the upper left and upper right of the rotor 2 as shown in FIG. 1 may also perform a portion of the rotor-lifting work during operation, the two upper radial actuators 12 may be configured to generate a larger magnetic field than the two lower radial actuators 12. For example, the two upper radial actuators 12 shown in FIG. 1 may optionally also include a permanent magnet for passively lifting the rotor 6. However, all radial actuators 12 may be configured the same or substantially the same in other embodiments.

In another alternate embodiment, if the lift actuator 10 is designed to lift, e.g., more than the weight of the rotor 6, then the two lower radial actuators 12 may be larger in order to be able to pull down the rotor 6 away from the lift actuator 10.

The radial actuators 12 may be mounted on the gantry housing equidistantly or substantially equidistantly around the circumference of the rotor 6 or in another arrangement. In the embodiment shown in FIG. 1, the radial actuators 12 are disposed in pairs that are separated by 180° from each other around the circumference of the rotor 6. The skilled person will recognize that various other configurations for the radial actuators 12 are possible depending upon the particular application of the present teachings and it is not necessary for radial actuators 12 to be oppositely disposed from each other.

Although not shown in FIG. 3, the magnetic flux path extends in a closed path, e.g., a substantially circular path, that extends generally in the X-Y plane (i.e. perpendicular to the view of FIG. 3) and goes through the stator core 20, across a clearance between the stator core 20 and the rotor 6 and though the adjacent portion of the rotor 6.

The embodiment of FIGS. 1-4 also includes three axial actuator pairs 14 mounted on the gantry housing. Two upper axial actuator pairs 14 are preferably disposed in a mirror-symmetric manner about a Y-Z plane that contains the ideal rotational axis 8'. The third axial actuator 14 is disposed at or near a bottom or vertically lowermost portion of the rotor 6. However, it should be understood that the axial actuators 14 need not be disposed in pairs and/or the upper axial actuator pairs 14 need not be disposed in a mirror-symmetric manner. Further, more or less than three axial actuators 14 can be used in certain embodiments of the present teachings.

Figure 4:
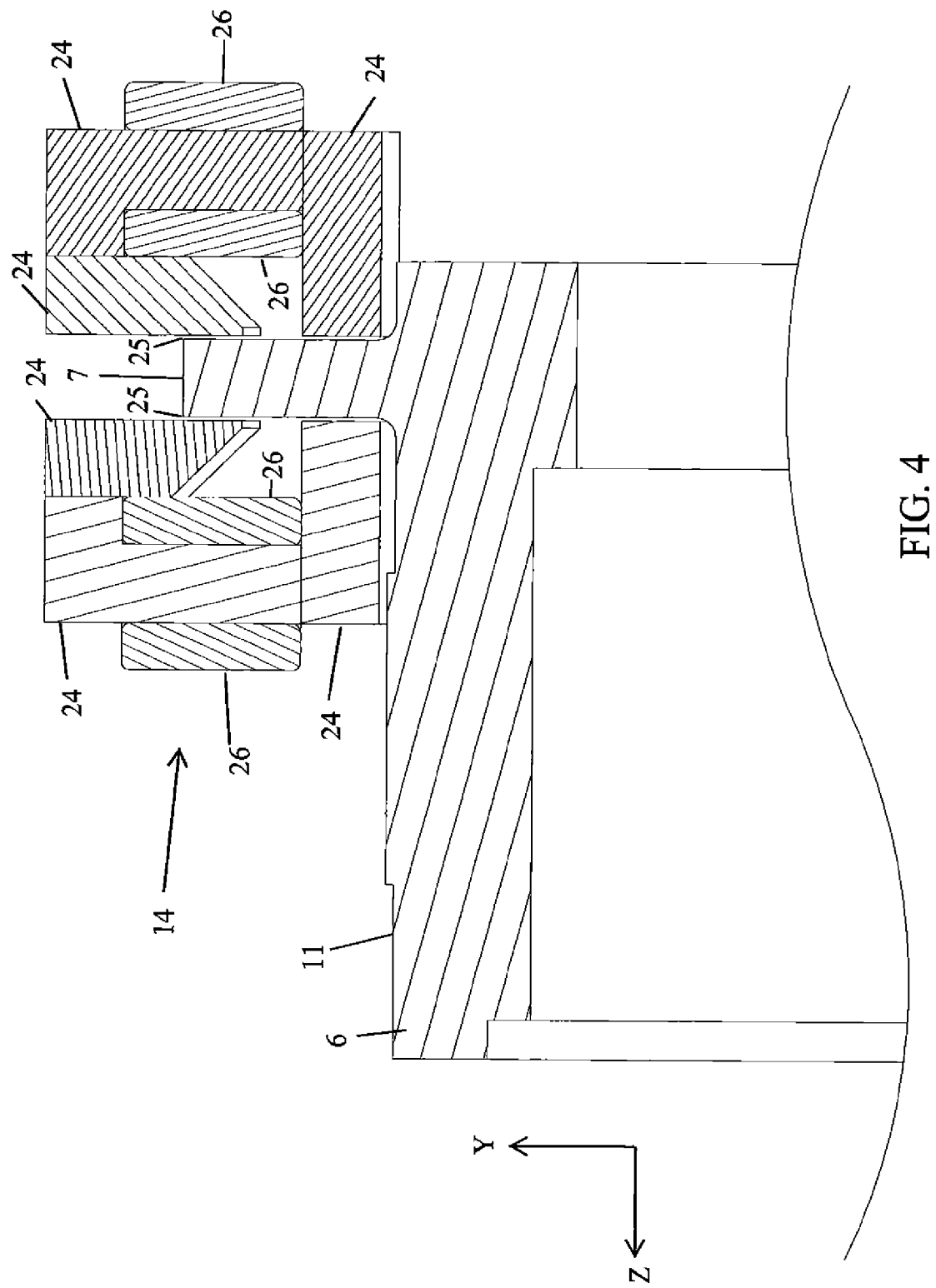
FIG. 4 shows a detailed cross-sectional view of an axial actuator shown in FIG. 1 and FIG. 5.

Referring to FIG. 4, a representative axial actuator pair 14 comprises a pair of stator cores 24, each having a coil 26 wound around it. The two sets of core 24 and coil 26 are disposed substantially in parallel with a spacing therebetween and are mounted on the gantry housing such that an annular flange 7 of the rotor 6 preferably extends in the radial direction within at least a portion of the radially-extending spacing.

The axial actuator pairs 14 are configured to variably adjust the position of the rotor 6 along the Z-direction, i.e. in the axial direction of the rotating rotor 6. That is, the axial actuators 14 are preferably individually controlled, i.e. the strength of the magnetic field generated by each respective set of stator core 24 and coil 26 is varied, so as to maintain the annular flange 7 substantially in the middle of the spacing between the pair of cores 24 and coils 26. For example, if the annular flange 7 (and thus the rotor 6) has drifted too far to the right in FIG. 4 (which corresponds to the rotor 6 moving into the page away from the viewer in the illustration of FIG. 1), the axial actuator pair 14 is controlled so that the force on the left side is greater than on the right side of FIG. 4, thereby pulling the annular flange 7 (and thus the rotor 6) to the left in FIG. 4.

Naturally, the design of the axial actuator 14 also may be modified without departing from the scope of the present teachings. For example, the cores 24 and coils 26 are not required to be disposed directly across from each other, such that a radially-extending spacing is defined between two sets of opposing cores 24 and coils 26. Instead, each set of one core 24 and coil 26 may be disposed around the circumference of the rotor 6 without a directly-opposing core 24 and coil 26. Furthermore, it is not necessary that equal numbers of cores 24 and coils 26 are disposed on opposite sides of the annular flange 7 in the Z-direction. However, it is generally preferred that at least one set of core 24 and coil 26 is disposed on each side of the annular flange 7 as viewed in the Z-direction, so as to enable the rotor 6 to be pulled or attracted by at least one actuator 14 in both directions along the Z-axis. Moreover, while homopolar axial actuators 14 are shown, heteropolar axis actuators could also be utilized.

Although not shown in FIG. 4, the magnetic flux path extends in a closed path, e.g., a substantially oval path, that extends generally in the Y-Z plane and goes through the various portions of the stator core 24, across the clearance 25 between the stator core 24 and the annular flange 7 and through the adjacent portion of the annular flange 7.

Also, the gap between the outer circumference 11 of the rotor 6 and the stator cores 24 of the axial actuator pair 14 is not necessarily shown to scale and may be relatively larger. In this case, the axial actuator pair 14 may be moved outward in the radial direction and the annular flange 7 may be extended farther in the radial direction so as to accommodate the larger gap between the rotor 6 and the cores 24.

Referring again to FIG. 1, at least one position sensor 9 is preferably disposed on the gantry housing around the circumference of the rotor 6. In this embodiment, four substantially equally-spaced position sensors 9 are utilized.

Each position sensor 9 is preferably configured to sense or detect the location of the rotor 6 in the X-Y (vertical) plane (radial direction) and/or along the Z-axis (axial direction). The position sensor(s) 9 is/are preferably non-contacting, inductive-type position sensors arranged in pairs to sense both axial and radial movement of the rotor 6. The signals generated by the position sensor(s) 9 are preferably transmitted to the magnetic bearing controller, which processes the signals and then adjusts the respective magnetic fields of at least the radial and axial actuators 12, 14 in order to correct any positional deviations of the rotor 6 from the ideal rotational axis 8' and/or the ideal position in the axial (Z) direction.

In addition, one or more auxiliary, non-magnetic bearings 28 are preferably mounted on the gantry housing for rotatably supporting the rotor 6, e.g., as a fail-safe in the event of a system fault or a power outage. In a further optional embodiment, one or more of the auxiliary bearings 28 may also perform a part of the function of rotatably supporting the rotor 6 during operation, although it is preferred that the actuators 10, 12, 14 perform all of the rotor-supporting work during operation so that the rotation of the rotor 6 is friction-free.

The auxiliary bearing(s) 28 may be embodied as one or more plain bearings, e.g., sleeves, bushings or journals, or may be one or more rolling-element bearings, e.g., ball bearings, angular contact bearings or cylindrical roller bearings. The auxiliary bearing(s) 28 may continuously extend all the way around the circumference of the rotor 6, e.g., the auxiliary bearing 28 may be embodied as a single, large bearing that completely encircles and rotatably supports the entire rotor 6. In the alternative, the auxiliary bearing 28 may comprise one or more individual elements, such as discrete ball bearings 28 as shown in FIG. 1 or discontinuous sections of a plain bearing. Optionally, the auxiliary bearing(s) may also include one or more radial air bearings.

As indicated in FIG. 1, the auxiliary bearings 28 optionally may be embodied as deep-groove ball bearings 28 mounted to the gantry housing and may be disposed in a mirror-symmetric manner about a Y-Z plane that contains the ideal rotational axis 8'. However, it is understood that the auxiliary bearings 28 also may be disposed equidistantly about the rotor 6 or as shown in FIG. 1 with the upper and lower auxiliary bearings 28 being relatively closer to each other.

It is also preferred that the auxiliary bearing(s) 28 has/have a radially-inward-facing bearing surface with a inner diameter that is slightly greater than an outer diameter of a radially-outermost portion of the rotor 6, which is disposed adjacent the radially-inward-facing bearing surface of the auxiliary bearing(s) 28. Thus, in normal operation, the slight difference in diameters means that no portion of the rotor 6 contacts the auxiliary bearing(s) 28 while the rotor 6 is rotating. However, in the event, e.g., that one or more of the actuators 10, 12, 14 malfunction(s), an outer portion of the rotor 6 may safely contact the auxiliary bearing(s) 28 and the auxiliary bearing(s) 28 will support the rotation of the rotor 6 at least temporarily, e.g., while the rotor 6 is slowing down.

Herein, it is noted that the width of the annular gap in the radial direction between the outer circumference 11 of the rotor 6 and the auxiliary bearing(s) 28 mounted on the stationary gantry housing is preferably less than the width of the annular gap in the radial direction between the outer circumference 11 of the rotor 6 and the lift actuator(s) 10, the radial actuator(s) 12 and/or the position sensor(s) 9 mounted on the stationary gantry housing. In this case, the lift actuator(s) 10, the radial actuator(s) 12 and/or the position sensor(s) 9 is/are prevented from ever contacting the rotor 6, thereby protecting these components, e.g. in the event of a system malfunction. In a preferred embodiment, the width of the annular gap relative to the auxiliary bearing(s) 28 may be, e.g., about one-half of the width of the annular gap relative to the lift actuator(s) 10, the radial actuator(s) 12 and/or the position sensor(s) 9.

In addition or in the alternative, it may be appropriate to also place one or more auxiliary bearings on each axial side of the annular flange 7 and/or on each axial side of the main body of the rotor 6, which auxiliary bearings would bound or limit the range of movement of the rotor 6 in the axial or Z direction. In this embodiment as well, the width of the gap or spacing in the axial direction between such auxiliary bearing(s) and the annular flange 7 and/or the main body of the rotor 6 is preferably less than the width of the gap 25 between each side of the axial actuator pair 14 and the annular flange 7, more preferably about one-half of width of the gap 25. In this case, the axial actuator(s) 14 (in particular the stator core 24) would be prevented from ever contacting the rotor 6. Such auxiliary bearing(s) may be selected from any of the auxiliary bearings described herein, such as, e.g., plain bearings or rolling-element bearings. In a preferred embodiment discussed further below, a linear or curved bearing attached to one of the gantry housing or the rotor 6 may function, e.g., together with a ring shaft attached to the other of the gantry housing or the rotor 6, to limit or bound, at least partially, movement of the rotor 6 in the axial or Z-direction.

In preferred embodiments, the lift actuator 10 is a passive homopolar radial actuator having a rated force-generating capacity of between about 5-15 kN (kilonewtons), more preferably between about 7-12 kN, the radial actuators are active heteropolar actuators having a rated force-generating capacity of between about 1.5-5.5 kN, more preferably between about 2.5-4.5 kN, and the axial actuators are active heteropolar actuator pairs having a rated force-generating capacity of between about 1.5-6.0 kN, more preferably between about 2.5-5.0 kN. Such specifications would be suitable for a rotor 6 having a diameter of about one meter and a weight of about 1000 kg. Naturally, these specifications may be varied to adapt the present teachings to other applications.

A second representative computed tomography machine 1' will be described with reference to FIGS. 4-7. Only differences with respect to the first representative embodiment will be discussed in detail, such that elements or features that are the same for the two embodiments need not be further discussed. Further, although a radiation source 2 and radiation detector 3 are not shown in FIG. 5, it is understood that one or both devices 2, 3 also may be mounted on the rotor 6 of the second representative embodiment.

Figure 5:
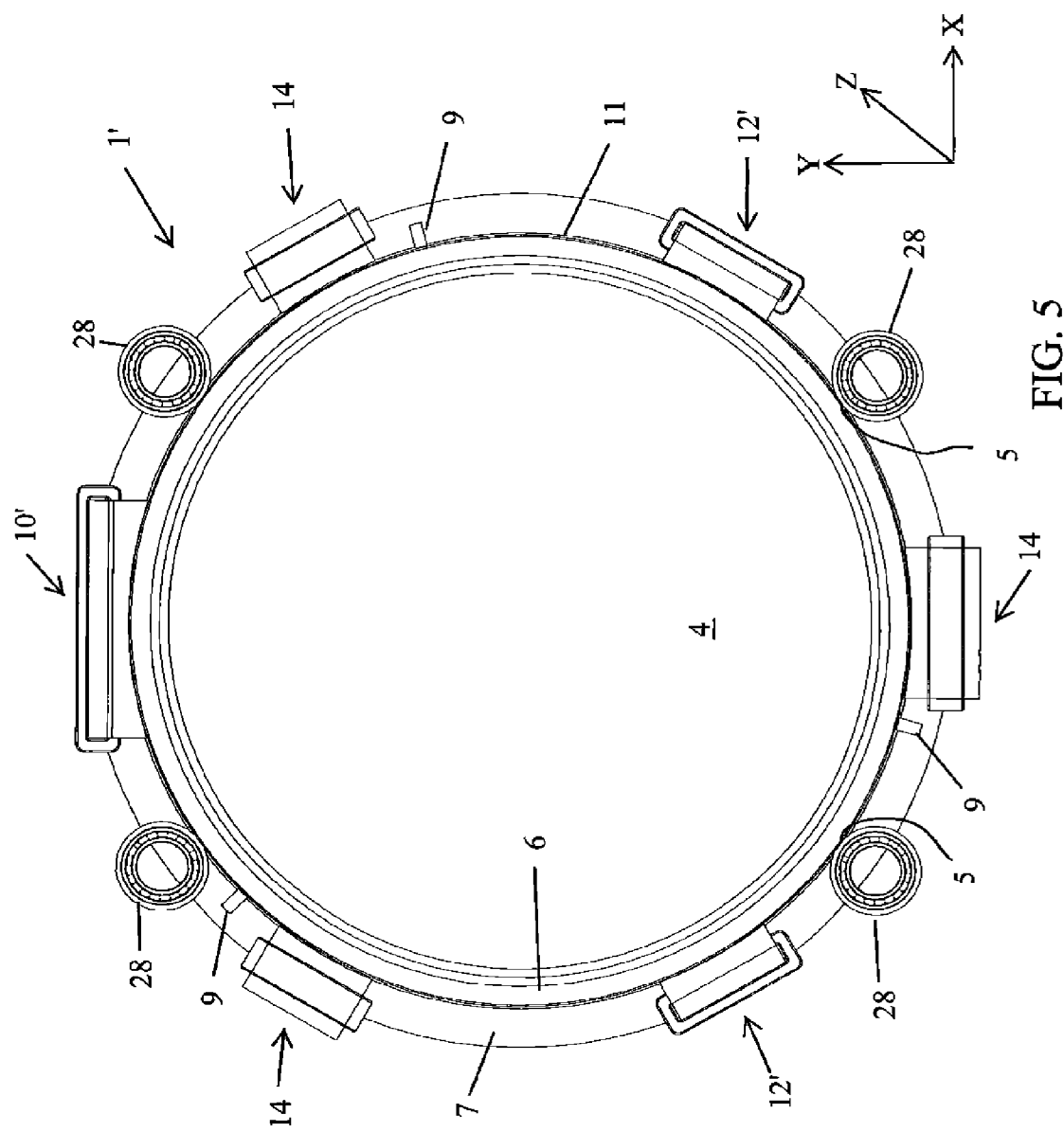
FIG. 5 shows an elevation view of a second representative embodiment of the present teachings.

FIG. 5 shows the computed tomography machine 1' in the X-Y plane. It is again understood that the Z-axis extends perpendicular to the sheet of the drawing. With respect to the arrangement of the actuators 10, 12, 14, the second representative embodiment differs from the first representative embodiment in that only two radial actuators 12' are provided around the lower half of the rotor 6, as the two upper radial actuators 12 shown in FIG. 1 have been omitted. Furthermore, only three position sensors 9 are utilized in the second representative embodiment instead of four and the upper and lower auxiliary bearings 28 have been spaced slightly farther apart than in FIG. 1.

Figure 6:
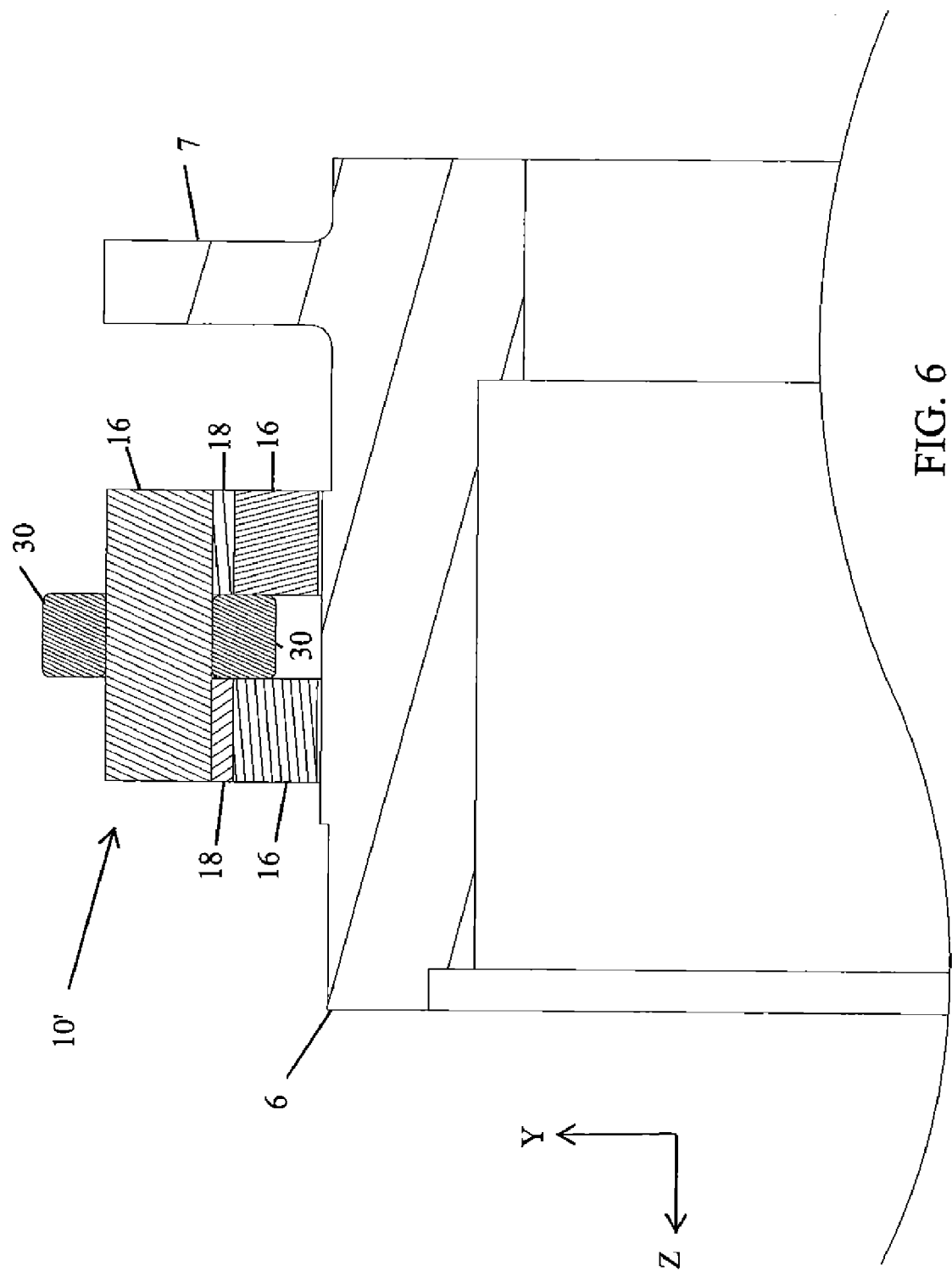
FIG. 6 shows a detailed cross-sectional view of a lift actuator shown in FIG. 5.

FIG. 6 shows a modified lift actuator 10' that may be utilized in either of the embodiments. This lift actuator 10' differs from FIG. 2 in that it contains a coil 30 wrapped around the stator core 16. Thus, the lift actuator 10' is an active actuator, which can generate a variable magnetic field in addition to the passive, permanent magnet field generated by the permanent magnet 18.

In such an embodiment, the electromagnet (coil 30 and core 16) may perform a portion of the rotor lifting work during operation, thereby supplementing the rotor-lifting force generated by the permanent magnet 18. However, in an alternate embodiment, the electromagnet may generate a field that cancels a portion of the magnetic flux generated by the permanent magnet 18.

The magnetic flux path of the lift actuator 10' of FIG. 6 extends in substantially the same manner as the magnetic flux path for the lift actuator 10 of FIG. 2.

Figure 7:
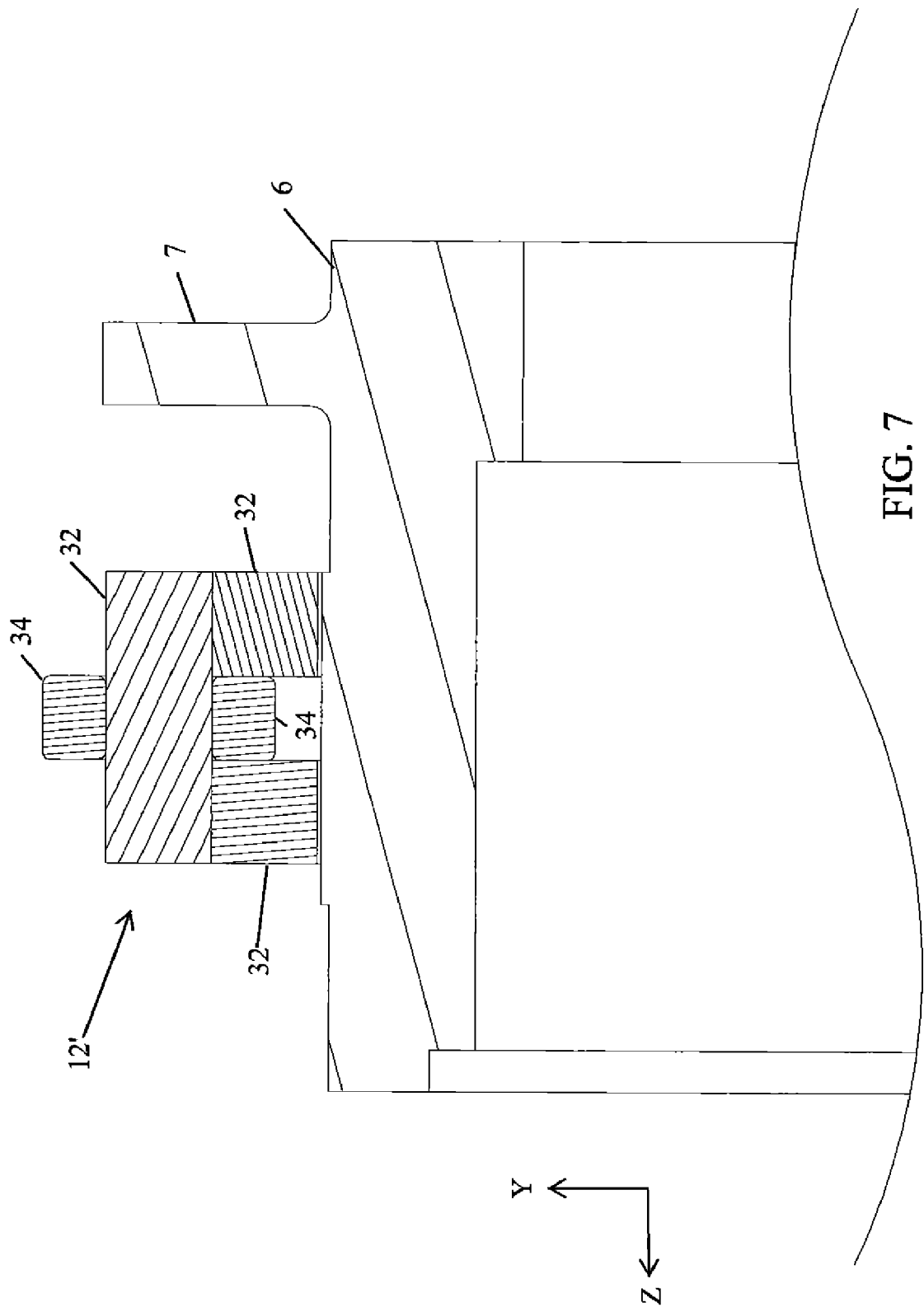
FIG. 7 shows a detailed cross-sectional view of a radial actuator shown in FIG. 5.

FIG. 7 shows a modified radial actuator 12' that also may be utilized in either of the embodiments. In FIG. 7, the coil 34 is wrapped around the stator core 32 in the X-Y plane.

In the radial actuator 12' of FIG. 7, the magnetic flux path extends in a closed path, e.g., a substantially circular path, that extends generally in the Y-Z plane and goes through the various portions of the stator core 32, across the gap between the stator core 32 and the rotor 6 and though the adjacent portion of the rotor 6.

The axial actuator 14 of FIG. 4 may be utilized in the second representative embodiment without modification. In the alternative, the axial actuator 14 may be heteropolar.

The following description is applicable to both the first and second representative embodiments, as well as modifications thereof.

The inner diameter of the hollow interior 4 of the rotor 6 is preferably about one meter, although larger or smaller diameters may be appropriate depending upon the particular application of the present teachings. Further, the system 1, 1' is preferably designed to permit rotational speeds of about 300 revolutions per minute, although faster or slower speeds are also encompassed by the present teachings. For example, rotational speeds of up to about 1200 revolutions per minute or even up to 2000 revolutions per minute are contemplated in certain embodiments of the present teachings.

The stator cores of the various actuators are preferably laminated homopolar cores, but solid cores and/or heteropolar cores are also contemplated. The first representative embodiment of FIGS. 1-4 preferably uses a mixture of homopolar and heteropolar actuators, whereas the second representative embodiment of FIGS. 5-7 may use all homopolar actuators. Generally speaking, it is understood that solid cores and rotors have lower manufacturing costs, but laminated cores and rotors provide performance advantages. The skilled person is free to select the most appropriate actuators based upon the particular application of the present teachings.

The rotor 6 may also be solid or laminated. In one embodiment, a laminated rotor 6 may be used with heteropolar radial actuators, which would provide high dynamic control.

The actuators 10, 12, 14 may be controlled using standard magnetic bearing controllers known in the art, which generally provide ten amplifiers for ten actuators. For example, the actuator control may be performed by a magnetic bearing controller available from SKF, Inc. having model no. MB4160.

A representative control process may begin with measurement of the rotor position in both the radial and axial directions using the position sensors 9. The signals from sensors 9 are transmitted to the magnetic bearing controller, which compares the signals to one or more values representing the ideal position of the rotor 6 in the radial and axial directions. The ideal position may be programmed or input into the controller during machine start-up or initialization, or dynamically during machine operation. Any difference between the actual position and the ideal position results in the calculation of the change in current or force necessary to pull the rotor back to the ideal position. This calculation is translated into a command to the power amplifiers respectively connected to the coils of the respective actuators. The command may preferably comprise an instruction to increase or decrease current flow to one or more of the respective coils. If the current to a particular coil is increased, magnetic flux through the actuator and adjacent portion of the rotor increases, thereby increasing the force between the rotating and stationary components. As a result, the rotor will move toward the particular actuator along the axis of control. Application of differing magnetic fluxes to the rotor 6 will be additive in the different directions with the direction of movement of the rotor 6 corresponding to a vector thereof.

Although a single lift actuator 10, 10' is shown in the two representative embodiments, it is understood that the lift actuator function could be separated into two or more lift actuators 10, 10'. For example, two lift actuators 10, 10' could be mounted to an upper half of the gantry housing in a mirror-symmetric manner about a Y-Z plane containing the ideal rotational axis 8'. The resulting lift vector generated by the two lift actuators 10, 10' is thus preferably in the vertical or substantially vertical direction.

For point of reference, representative, but non-limiting dimensions for various elements of a representative CT machine 1 will be provided. For example, the rotor 6 preferably may have a radial width of about 25 millimeters and a depth in the Z-direction of about 81 millimeters. The stator cores 24 of the axial actuators 14 may have a radial width of about 50 millimeters and a depth in the Z-direction of about 30 millimeters. The gap 25 (see FIG. 4) between the stator core 24 and the annular flange 7 is preferably or ideally maintained during operation at about one millimeter on each side of the annular flange 7 in the Z-direction. The lift and/or radial actuators 10, 12 preferably may have a radial width of about 57 millimeters and a depth in the Z-direction of 60 millimeters.

The actuators 10, 10', 12, 12' preferably have a curvature on the side facing the rotor 6 that corresponds to the outer contour of the rotor 6, i.e. the rotor-facing sides are semi-circular. This means that the rotor-facing side of the magnet and/or the stator core is preferably semi-circular. The axial actuator 14 is preferably straight, although curved configurations are also possible.

The bearing and sensor surfaces on the rotor 6 may be laminated and/or solid. The rotor 6 may be constructed as a single, integral component (i.e. a one-piece construction) or may be an assembly of several pieces, each comprised of magnetic and/or non-magnetic materials.

The first and second representative embodiments provide five axes of active control. In the alternative, one or more of the axes may be levitated passively (i.e. no active control) or may be controlled mechanically with a permanently-engaged rolling element, sliding or air/hydrodynamic bearings or any other type of bearing(s).

At least the radial and axial actuators 12, 14 (as well as the lift actuator 10 if it has an electromagnet) are preferably controlled according to a closed loop feedback using signals from the position sensors 9 to adjust the gantry/rotor position. As non-limiting examples, the control may be based upon independent axis control (SISO—single input, single output) or combined axis control (MIMO—multiple input, multiple output).

While all of the actuators 10, 12, 14, sensors 9 and auxiliary bearings 28 are shown as generally falling within a single X-Y plane, naturally the various components may be located in two or more X-Y planes, each separated by an axial distance. If multiple vertical planes of components are utilized, each vertical plane may have the same, less or more components (e.g., bearings, sensors, etc.) as any other plane.

The system 1 may include an integrated rotational motor, with or without electrical contacts (e.g., brushes) between the rotor 6 and the stationary components.

An uninterrupted power supply may be utilized to improve system robustness.

The present teachings also may be easily modified for an annular rotor 6 that is rotated about a vertical or a substantially vertical rotational axis, which means that the rotational plane of the rotor 6 is horizontal or substantially horizontal. In this case, at least one lift actuator is disposed above the annular rotor to vertically lift the annular rotor at least while it rotates. For example, two or more lift actuators may be disposed substantially equidistantly away from each other around the outer circumference of the annular rotor 6 or the annular flange 7. Because the lift actuators influence the position of the rotor 6 in its axial direction (i.e. the axial direction of the rotor 6 extends in the vertical direction), the lift actuators may preferably perform at least a part of the function of the above-described axial actuators 14 and may be constructed in substantially the same way as the axial actuator 14 of FIG. 3, although it is preferred that at least one permanent magnet is provided on the vertically upper side of the rotor 6 in order to provide passive lifting capacity, which would improve the overall system efficiency.

Thus, the lift actuators may be combined with the axial actuators, such that one or more pairs of actuators are provided, preferably equidistantly around the circumference of the annular rotor 6. As a result, the lift/axial actuators of such an embodiment would be capable of pulling the rotor 6 up and down in the vertical direction.

In such an embodiment, at least one radial actuator influences the position of the rotor 6 in the radial direction of the rotor 6. Again, it is preferable to dispose at least three radial actuators around the outer circumference of the rotor 6 and such radial actuators may be constructed in a similar fashion to the radial actuators 12, 12' of FIGS. 3 and 7.

In another modification of the present teachings, one or more of the magnetic actuators 10, 10', 12, 12', 14 may be replaced by a non-magnetic bearing. For example, it would be possible to use magnetic bearings for controlling the position of the rotor 6 in its axial direction, while non-magnetic bearings (e.g., bushings or rolling-element bearings) rotatably support the outer circumferential surface of the rotor 6 in the radial direction thereof. In addition or in the alternative, the rotor 6 may be axially supported or guided by one or more non-magnetic bearings and magnetic bearings may be used to rotatably support the rotor 6 in the radial direction during operation. Thus, in certain embodiments, one or more of the lift actuator, radial actuator and/or axial actuator (axial actuator pair) may be replaced with any one or more of the non-magnetic bearings that are disclosed herein above or below. For purposes of conciseness, it is understood that any of the non-magnetic bearings disclosed herein are suitable replacements for the lift, radial and/or axial actuators (magnetic bearings) and all respective combinations of magnetic and non-magnetic bearings are disclosed hereby.

The present teachings are not particularly limited to CT machines and may be preferably utilized with any rotor application, in which the rotational axis of the rotor 6 is substantially in the horizontal or vertical plane, although various degrees of tilting therefrom are also contemplated. The rotor 6 may be solid or substantially solid or the rotor 6 may be tubular, e.g., it may have an at least partially hollow interior.

Although the preferred radiation source for the computed tomography image system is an x-ray source, other radiation sources and corresponding detectors may be utilized to achieve, for example, positron emission tomography, electron beam tomography or single photon emission computed tomography. Further, other sources of radiation may be attached to the rotor for other applications, such as sources of ionizing or non-ionizing radiation, including e.g. lasers. The present teachings are widely applicable to any application that utilizes a high-speed rotor to carry a device that operates in a non-contacting manner while being rotated relative to a target object.

Although a variety of non-magnetic auxiliary bearings 28 may be utilized as a 'back up' in case of a system or a power failure, as was described above, another possibility is a linear bearing, such as a linear ball bearing available from SKF, Inc. under model number LBBR25. In principle, the function of the auxiliary bearing(s) 28 is to prevent the rotor 6 from ever directly contacting the gantry housing and also to at least temporarily support rotation of the rotor 6 in case the rotating rotor 6 unintentionally touches the bearing(s) 28 during operation or when the system is not functional (e.g., power off). For example, if one or more of the magnetic actuators 10, 10', 12, 12', 14 fails to function properly during operation, there will be no damage to the rotor 6 caused by the moving rotor 6 contacting the stationary housing, because the rotor 6 will be rotatably supported by the auxiliary bearing(s) 28 at least temporarily.

A linear ball bearing generally involves a tubular housing structure, e.g., a bushing, having a plurality of closed-loop grooves, e.g., recirculating ball tracks, formed or defined on an inner surface thereof or formed in a bearing cage disposed within the bushing. Each closed-loop groove has a pair of parallel grooves or tracks extending in the longitudinal direction of the linear bearing. The straight grooves or tracks are connected at each end by a curved, e.g., semi-circular, groove or track, e.g., a deflection track. Ball bearings are rotatably and movably disposed within each of the closed-loop grooves and support a cylindrical shaft that extends through the tubular structure. When the cylindrical shaft moves in the longitudinal direction of the linear bearing relative to the tubular structure, the ball bearings circulate around each closed-loop groove or track. The ball bearings on one longitudinal side of the closed-loop groove support the linear movement of the cylindrical shaft and act as load-bearing balls. The ball bearings on the other longitudinal side of the closed-loop groove do not support the load (i.e. non-load-bearing balls) and move in the opposite direction of the movement direction of the cylindrical shaft. Therefore, the depth on the non-supporting longitudinal side of the closed-loop groove is deeper than on the load-bearing longitudinal side. The bearing balls disposed on the non-load bearing side are not required to be exposed to the inner surface of the tubular surface and, e.g., may be covered by a metal plate structure.

In addition, the load-bearing side of the closed-loop groove may be reinforced with a load or track plate, e.g., a metal plate structure, disposed between the ball bearings and the tubular housing structure. Further, the tubular housing structure may be hardened plastic or metal, preferably metal, such as steel in the presently preferred applications.

Further teachings concerning a representative linear bearing can be found in U.S. Pat. No. 6,168,313, which is incorporated herein by reference.

In a further embodiment of the present disclosure, a torus-shaped or toroidal structure, preferably a ring torus, is mounted to one of the rotor 6 or the gantry housing. Linear ball bearings may be mounted to the other of the rotor 6 and the gantry housing. The torus-shaped structure extends through the linear ball bearings and is preferably comprised of a metal. The torus-shaped structure may be a hardened wire structure.

It is preferred that the linear ball bearings are mounted onto the rotor 6 so as to rotate therewith. In this case, the shaft of the torus-structure is fixedly mounted on or attached to the gantry housing and the shaft has an outer diameter that is slightly smaller than the inner diameter of the linear ball bearing. Preferably, the outer diameter of the shaft is selected such that the annular gap or clearance between the shaft of the torus structure and each longitudinal end of the linear bearing is smaller than the gap between the rotor and the magnetic bearings/actuators, i.e. when the magnetic bearings are levitating and rotatably supporting the rotor 6. During normal operation, the torus-shaped structure preferably does not contact the linear ball bearings so as to permit friction-free rotation of the rotor 6.

Although the balls of the linear ball bearing may be metal, such as steel, it is preferred that the balls comprise or substantially consist of a ceramic material, e.g., bearing-grade silicon nitride. In addition, the ball recirculation mechanism of the linear ball bearing is preferably reinforced to such a degree as to allow for the instantaneous acceleration from zero to 10 meters per second in case the torus-shaped structure comes into contact with the linear ball bearings, i.e. touches down, while the rotor 6 is rotating at top speed, e.g., about 300 revolutions per minute, although other top rotational speeds are contemplated.

Figure 8B:
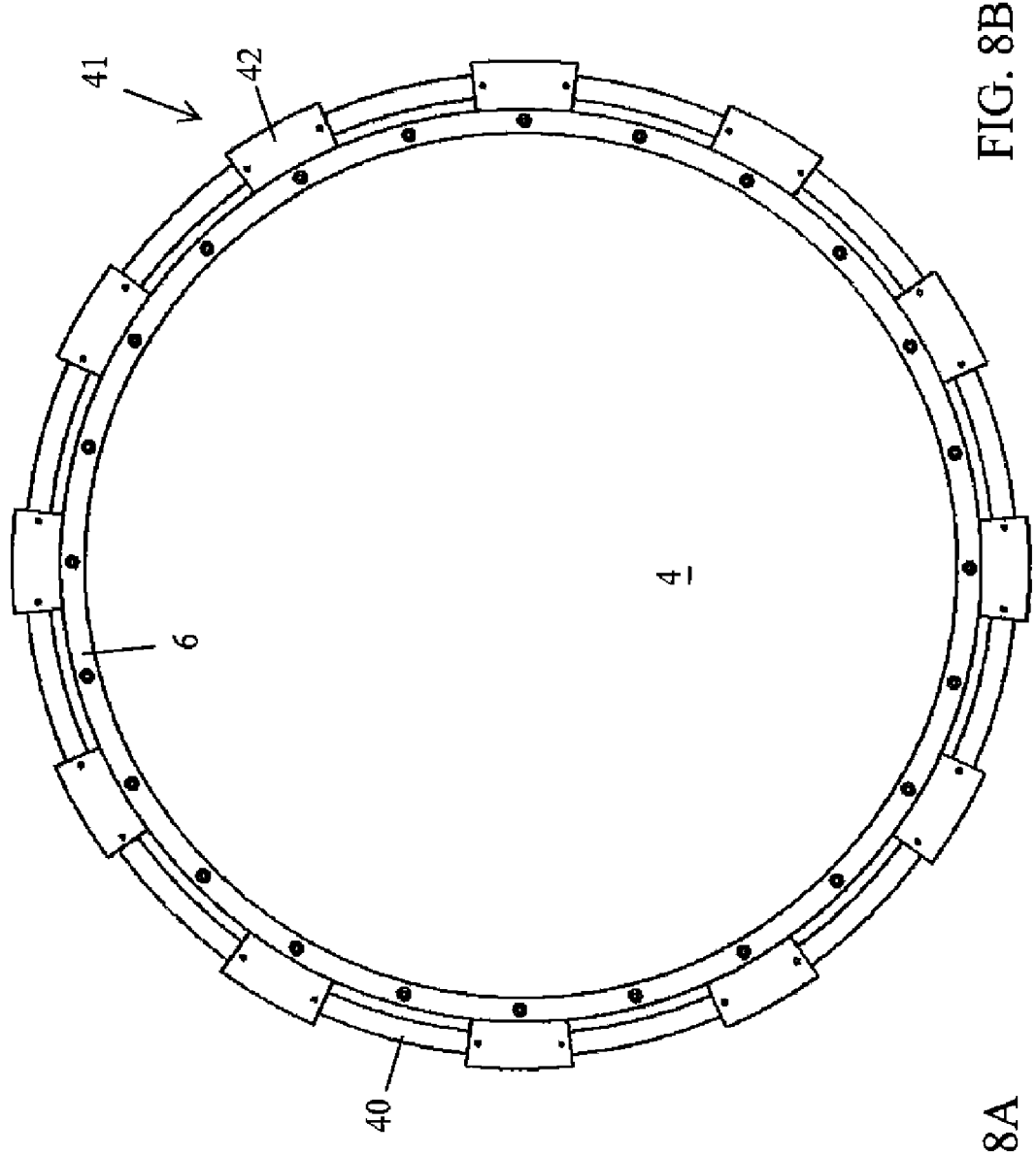
FIG. 8B shows an elevation view of the curved bearing arrangement as viewed along the axial direction of the annular rotor.
Figure 8A:
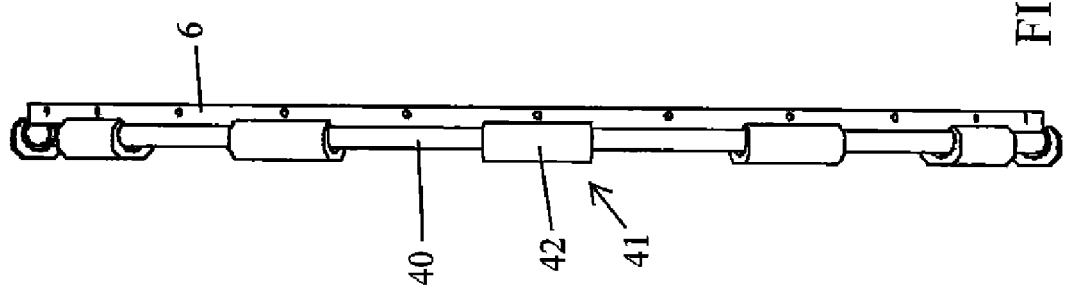
FIG. 8A shows a side view of a representative curved bearing arrangement for supporting or supplementally supporting an annular rotor.
Figure 10:
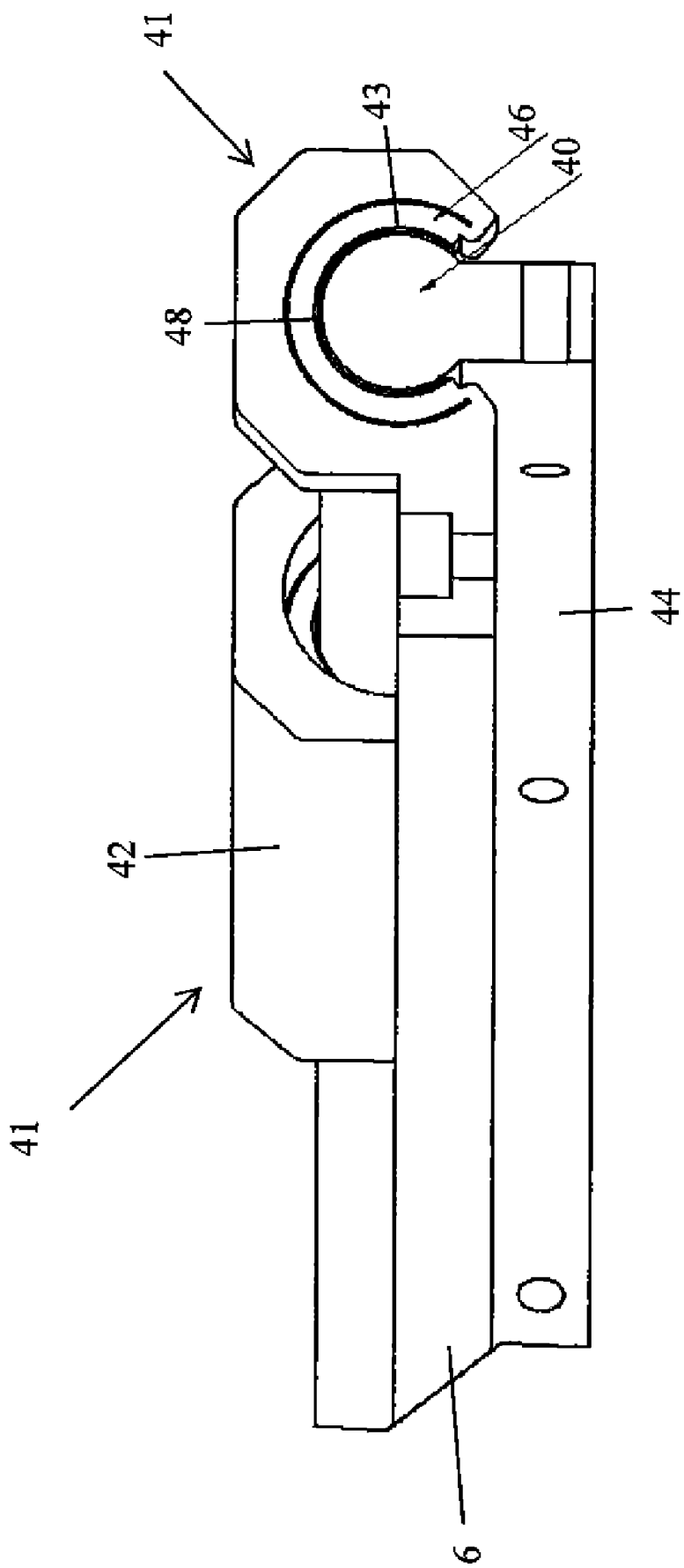
FIG. 10 shows another perspective view of a portion of the curved bearing arrangement of FIGS. 8A and 8B.

In a modification of the above-described linear ball bearing embodiment, the tubular housing structure 42 supporting the balls may be curved, thereby forming a curved, tubular ball bearing 41 as shown in FIGS. 8-10. The curved tubular housing structure 42 preferably has the same, or substantially the same, curvature as a generally torus-shaped shaft 40 movably disposed therein. Further, the shaft 40 preferably has an outer diameter that is slightly less than an inner diameter of the ball bearing cage 46 so that an annular clearance 48 is present between the shaft 40 and the inner surface 43 of the curved bearing 41 when the rotor 6 is being rotated under the guidance of the above-describe magnetic bearing system. During normal operation, the annular clearance 48 is preferably at least substantially constant along the entire length of each curved bearing 41 and the portion of the shaft 40 disposed therein.

A plurality of curved bearings 41 (e.g., twelve as shown in FIG. 8B) may be affixed to the rotor 6 in equally-spaced intervals. The shaft 40 is movably supported by the curved bearings 41 and is affixed to the stationary gantry housing via an annular connecting flange 44 (see FIGS. 9-10). The connection of the flange 44 and thus the shaft 40 to the stationary gantry housing is not shown in the drawings for purposes of simplicity and clarity.

However, it should be understood that this bearing/shaft arrangement may be reversed such that the shaft 40 is affixed to the rotor 6 so as to rotate therewith and the curved bearings 41 are affixed to the stationary gantry housing.

In another modification of the above-described linear ball bearing, the grooves or tracks of the bearing cage 46 of the curved bearing 41 may be designed such that the non load-bearing ball path is disposed radially outward of the load-bearing ball path, instead of curving around the circumference of the shaft 40. For example, a metal load plate, which provides support for the load-bearing balls, may be disposed between the load-bearing balls and the non load-bearing balls. In this case, after supporting the load (i.e. contacting the ring shaft 40), the balls would circulate or move along a first curved path that is directed radially outward from the load-bearing path, then along the non-load bearing path (disposed directly radially outward of the load-bearing path) and finally along a curved path extending radially inwardly to reach the load-bearing path again. Thus, the balls would move up a ramp to come into contact again with the ring shaft 40, instead of moving around a corner or curved path as is typical in linear bearings. In this embodiment, the load-bearing path and non load-bearing path are preferably both curved and the two curves are preferably concentric. The two curves are also disposed in the same plane, which extends in the radial direction of the rotor 6.

The non load-bearing path may be configured substantially as a curved tube defined within the tubular structure, which is again preferably constructed from a metal material, such as steel.

The roller bodies optionally may be cylindrical in such an embodiment.

In a further modification of either of the above-described linear and curved ball bearings, the linear or curved ball bearing is not required to be enclosed in the circumferential direction. Rather, as shown most clearly in FIG. 10, an opening of about 100°, e.g., between 90-120°, may extend along one longitudinal side of the curved or linear bearing, e.g. along a side opening towards the axial or Z-direction of the rotor 6. Such an opening would permit the ring shaft 40 to be easily mounted in and removed from the curved or linear bearing by moving the shaft 40 in the axial or Z-direction of the rotor 6. For example, the opening may be sized so that the ring shaft 40 snap-fits through the opening in the side of the curved or linear bearing when the ring shaft 40 is mounted in the curved or linear bearing. Thus, the size of the opening in the circumferential direction of the curved or linear bearing is preferably slightly smaller than the outer diameter of the ring shaft 40.

If a curved bearing 41 is provided with such a side-opening, the bearing cage 46 is preferably provided with five closed-loop ball circulation paths, such that there are five load-bearing ball tracks for contacting the ring shaft 40. Such a curved bearing 41 preferably has a static load capacity of about 1500 Newtons for the above-described CT application. In a further embodiment, two curved ball bearings 41 may be utilized at each bearing point and the bearing points may be spaced approximately 15° apart, thereby providing twelve bearing points around the circumference of the rotor 6. Each bearing cartridge 41 may have a length of approximately 15-30 centimeters, more preferably 20-25 centimeters, although the particular length will depend upon application-specific parameters.

REFERENCE NUMBER LIST

1, 1' Computed tomography machine
2 Radiation source
3 Radiation detector
4 Hollow interior of rotor 6
5 Annular gap 6 Rotor (annular gantry)
7 Annular flange
8 Rotational axis of rotor 6
8' Ideal rotational axis of rotor 6
9 Position sensor
10, 10' Lift actuator
11 Outer circumference of rotor 6
12, 12' Radial actuator
14 Axial actuator
16 Stator core
18 Permanent magnet
20 Stator core
22 Coil
24 Stator core
25 Spacing
26 Coil
28 Auxiliary bearing
30 Coil
32 Stator core
34 Coil
40 Ring shaft
41 Curved bearing
42 Curved tubular housing
43 Inner surface
44 Annular connecting flange
46 Bearing cage
48 Annular clearance

The invention claimed is:

1. A diagnostic scanning apparatus comprising:
an annular rotor configured to be rotated about a rotational axis, the rotor having (i) a hollow interior sized to receive a patient, (ii) a longitudinal length less than its diameter and (iii) a magnetically-permeable material disposed on or proximal to an outer circumference of the rotor,
a radiation source affixed to the rotor so as to rotate therewith,
at least one non-magnetic bearing disposed around the outer circumference of the rotor, and
a magnetic bearing system configured to influence the position of the rotor in three-dimensional space and including at least three actuators configured to generate a magnetic field that interacts with the magnetically-permeable material of the rotor, wherein:
at least one lift actuator generates a force for lifting the rotor in a vertical direction,
at least one radial actuator influences the position of the rotor in the radial direction of the rotor and at least assists in maintaining an annular gap between the rotor and the at least one non-magnetic bearing in a radial direction of the rotor while the rotor is rotating under control of the magnetic bearing system, and
at least one axial actuator influences the position of the rotor in an axial direction of the rotor.

2. A diagnostic scanning apparatus as in claim 1, wherein the rotor includes an annular flange comprising, at least in part, a magnetically-permeable material, the at least one axial actuator being disposed proximal to the annular flange.

3. A diagnostic scanning apparatus as in claim 2, wherein the at least one axial actuator comprises a pair of axial actuators, each configured to generate a variable magnetic field independent of the other, the annular flange being disposed within a radially-extending gap defined between the pair of axial actuators.

4. A diagnostic scanning apparatus as in claim 3, wherein the apparatus comprises at least three axial actuators fixedly disposed around the rotor and being spaced approximately equidistantly to each other.

5. A diagnostic scanning apparatus as in claim 4, wherein:
the rotational axis extends substantially in a horizontal direction,
the at least one lift actuator comprises at least one permanent magnet configured to lift at least 50% of the weight of the rotor and an electromagnet configured to generate a variable magnetic field, and
the at least one non-magnetic bearing is selected from a plain bearing and a rolling-element bearing.

6. A diagnostic scanning apparatus as in claim 1, wherein the apparatus comprises at least three axial actuators fixedly disposed around the rotor and being spaced approximately equidistantly to each other.

7. A diagnostic scanning apparatus as in claim 1, wherein the at least one lift actuator comprises at least one permanent magnet configured to lift at least 50% of the weight of the rotor.

8. A diagnostic scanning apparatus as in claim 1, wherein the at least one lift actuator comprises an electromagnet configured to generate a variable magnetic field.

9. An apparatus comprising:
an annular rotor having an annular flange and comprising, at least in part, a magnetically-permeable material disposed on or proximal to an outer circumference of the annular rotor and the annular flange, the rotor being rotatable about a rotational axis,
at least one non-magnetic bearing disposed adjacent to the annular rotor and capable of rotatably supporting the annular rotor at least temporarily, wherein the outer circumference of the annular rotor has a diameter slightly less than the diameter of a radially-inward-facing surface of the non-magnetic bearing and
a magnetic bearing system disposed adjacent to the outer circumference of the annular rotor, the magnetic bearing system comprising:
at least one lift actuator generating a magnetic field and being fixedly disposed adjacent to a vertically upper portion of the annular rotor, the at least one lift actuator being configured to generate a force that lifts the annular rotor in a vertical direction at least while the annular rotor is rotating about the rotational axis,
at least one radial actuator generating a variable magnetic field and being fixedly disposed adjacent to the outer circumference of the annular rotor, the at least one radial actuator being configured to influence the position of the annular rotor in the radial direction of the annular rotor while the annular rotor is rotating so as to maintain an annular clearance between the radially-inward-facing surface of the at least one non-magnetic bearing and the outer circumference of annular rotor, and
at least one axial actuator generating a variable magnetic field and being fixedly disposed adjacent to the annular flange, the at least one axial actuator being configured to influence the position of the annular rotor in an axial direction of the rotor.

10. An apparatus as in claim 9, wherein the at least one axial actuator comprises a pair of axial actuators, each configured to generate a variable magnetic field independent of the other, the annular flange being disposed within a radially-extending gap defined between the pair of axial actuators.

11. An apparatus as in claim 10, wherein the apparatus comprises at least three axial actuators fixedly disposed around the rotor and being spaced approximately equidistantly to each other.

12. An apparatus as in claim 9, wherein the rotational axis extends substantially in a horizontal direction.

13. An apparatus as in claim 9, wherein the at least one lift actuator comprises at least one permanent magnet configured to lift at least 50% of the weight of the annular rotor.

14. An apparatus as in claim 13, wherein the at least one lift actuator further comprises an electromagnet configured to generate a variable magnetic field.

15. An apparatus as in claim 9, wherein the apparatus comprises at least three radial actuators disposed around the outer circumference of the annular rotor.

16. An apparatus as in claim 9, wherein the at least one non-magnetic bearing is selected from a plain bearing and a rolling-element bearing.

17. An apparatus as in claim 9, wherein the rotor has an outer diameter that is greater than its longitudinal length.

18. An apparatus as in claim 17, wherein the rotor has a hollow interior sized to receive a patient therein.

19. An apparatus as in claim 18, wherein the apparatus is a diagnostic scanning apparatus and further comprises a radiation source mounted on the annular rotor so as to rotate therewith.

20. An apparatus as in claim 19, wherein:
the rotational axis extends substantially in a horizontal direction,
the at least one lift actuator comprises at least one permanent magnet configured to lift at least 50% of the weight of the annular rotor and an electromagnet configured to generate a variable magnetic field,
the at least one non-magnetic bearing is selected from a plain bearing and a rolling-element bearing, and
wherein the apparatus comprises:
at least three axial actuators fixedly disposed around the annular rotor, the annular flange being disposed within respective spacings defined in each of the axial actuators and
at least three radial actuators disposed around the outer circumference of the rotor.

21. An apparatus as in embodiment 20, further comprising a radiation detector mounted on the annular rotor generally opposite of the radiation source.

22. An apparatus comprising:
an annular rotor having an annular flange extending in a radial direction of the annular rotor, the annular rotor comprising, at least in part, a magnetically-permeable material on or adjacent to at least one circumferential surface and the annular rotor being rotatable about a rotational axis,
at least one non-magnetic bearing disposed adjacent an outer circumference of the annular rotor,
at least one radial actuator disposed adjacent to the outer circumferential portion of the annular rotor, the at least one radial actuator being controllable to influence the position of the annular rotor in a plane perpendicular to rotational axis while the annular rotor rotates so as to maintain an annular gap between the at least one non-magnetic bearing and the annular rotor, and
at least three axial actuators disposed around the circumference of the annular rotor in a spaced relationship relative to each other, the annular flange being disposed within a spacing defined in each of the axial actuators, each axial actuator comprising an electromagnet that is controllable to influence the position of the annular rotor in an axial direction of the annular rotor.

23. An apparatus as in claim 22, wherein the apparatus comprises at least three radial actuators disposed adjacent to the outer circumferential portion of the annular rotor in a spaced relationship relative to each other, wherein at least one of the radial actuators comprises at least one permanent magnet configured to vertical lift at least 50% of the weight of the annular rotor.

24. An apparatus as in claim 23, wherein the annular rotor has an outer diameter that is greater than its longitudinal length.

25. An apparatus as in claim 24, wherein the apparatus is a diagnostic scanning apparatus and further comprises a radiation source mounted on the annular rotor so as to rotate therewith.

26. An apparatus as in claim 22, wherein at least one of the actuators comprises a laminated core.

\* \* \* \* \*